(12) United States Patent
Kaur et al.

(10) Patent No.: US 10,531,825 B2
(45) Date of Patent: Jan. 14, 2020

(54) THRESHOLDING METHODS FOR LESION SEGMENTATION IN DERMOSCOPY IMAGES

(71) Applicants: Ravneet Kaur, Secunderabad (IN); William Van Dover Stoecker, Rolla, MO (US); Nabin K. Mishra, Glen Carbon, IL (US); Reda Kasmi, Bejaia (DZ)

(72) Inventors: Ravneet Kaur, Secunderabad (IN); William Van Dover Stoecker, Rolla, MO (US); Nabin K. Mishra, Glen Carbon, IL (US); Reda Kasmi, Bejaia (DZ)

(73) Assignee: Stoecker & Associates, LLC, Rolla, MO (US)

( * ) Notice: Subject to any disclaimer, the term of this patent is extended or adjusted under 35 U.S.C. 154(b) by 124 days.

(21) Appl. No.: 15/785,232

(22) Filed: Oct. 16, 2017

(65) Prior Publication Data
US 2018/0103892 A1    Apr. 19, 2018

Related U.S. Application Data

(60) Provisional application No. 62/408,603, filed on Oct. 14, 2016.

(51) Int. Cl.
*A61B 5/00*   (2006.01)
*G06T 7/136*   (2017.01)
(Continued)

(52) U.S. Cl.
CPC ............ *A61B 5/444* (2013.01); *A61B 5/0077* (2013.01); *G06T 7/0012* (2013.01); *G06T 7/11* (2017.01);
(Continued)

(58) Field of Classification Search
CPC ....... G06T 15/205; G06T 3/0093; G06T 3/20; G06T 7/32; G06T 7/70
(Continued)

(56) References Cited

U.S. PATENT DOCUMENTS

2006/0142983 A1 * 6/2006 Sorensen ............... A61B 5/055
703/11
2011/0228994 A1 * 9/2011 Tanaka ................. G06T 7/0012
382/128
(Continued)

FOREIGN PATENT DOCUMENTS

| AU | 2015307296 A | * 3/2016 | ............... A61B 5/00 |
| IN | 201641019473 | * 10/2016 | |
| WO | WO2016032398 | * 8/2014 | ............... A61B 5/00 |

OTHER PUBLICATIONS

U.S. Appl. No. 61/616,633, filed Mar. 2012, Zouridakis.*

*Primary Examiner* — Jerome Grant, II
(74) *Attorney, Agent, or Firm* — Faegre Baker Daniels LLP

(57) ABSTRACT

Systems and methods facilitate segmenting a dermoscopy image of a lesion to facilitate classification of the lesion. A dermoscopy image is received from an image source; pre-processed; and segmented. Segmenting the pre-processed dermoscopy image includes applying a thresholding algorithm to the dermoscopy image. The thresholding algorithm includes at least one of a Huang auto-thresholding algorithm, a Li auto-thresholding algorithm, a Shanbhag auto-thresholding algorithm, an Otsu auto-thresholding algorithm, or an Isodata thresholding algorithm. A weighted border error metric is provided to allow prediction of whether segmentation is likely to avoid excluding portions of the lesion. A test is provided for determination of whether image inversion is needed for the methods to provide optimal borders. An iterative expansion algorithm is pro-
(Continued)

vided to for determine whether expansion is needed for the methods to provide optimal borders and to determine the degree of expansion needed for more inclusive segmentation.

16 Claims, 15 Drawing Sheets
(8 of 15 Drawing Sheet(s) Filed in Color)

(51) Int. Cl.
    *G06T 7/00*     (2017.01)
    *G06T 7/11*     (2017.01)

(52) U.S. Cl.
    CPC .... *G06T 7/136* (2017.01); *G06T 2207/10024* (2013.01); *G06T 2207/20036* (2013.01); *G06T 2207/20076* (2013.01); *G06T 2207/20081* (2013.01); *G06T 2207/30088* (2013.01); *G06T 2207/30096* (2013.01)

(58) Field of Classification Search
    USPC .......................................................... 382/128
    See application file for complete search history.

(56) References Cited

U.S. PATENT DOCUMENTS

| | | | |
|---|---|---|---|
| 2014/0153807 A1* | 6/2014 | Seong | G06T 7/0016 |
| | | | 382/131 |
| 2014/0286551 A1* | 9/2014 | Yoshida | G06T 19/00 |
| | | | 382/128 |
| 2017/0023658 A1* | 1/2017 | Sun | A61B 5/055 |
| 2017/0061087 A1* | 3/2017 | Boroczky | G06F 19/321 |
| 2017/0258451 A1* | 9/2017 | Sakanashi | A61B 8/08 |
| 2018/0010197 A1* | 1/2018 | Beane-Ebel | C12Q 1/6886 |
| 2018/0038867 A1* | 2/2018 | Troisi | G01N 33/57442 |
| 2018/0103892 A1* | 4/2018 | Kaur | A61B 5/444 |

* cited by examiner

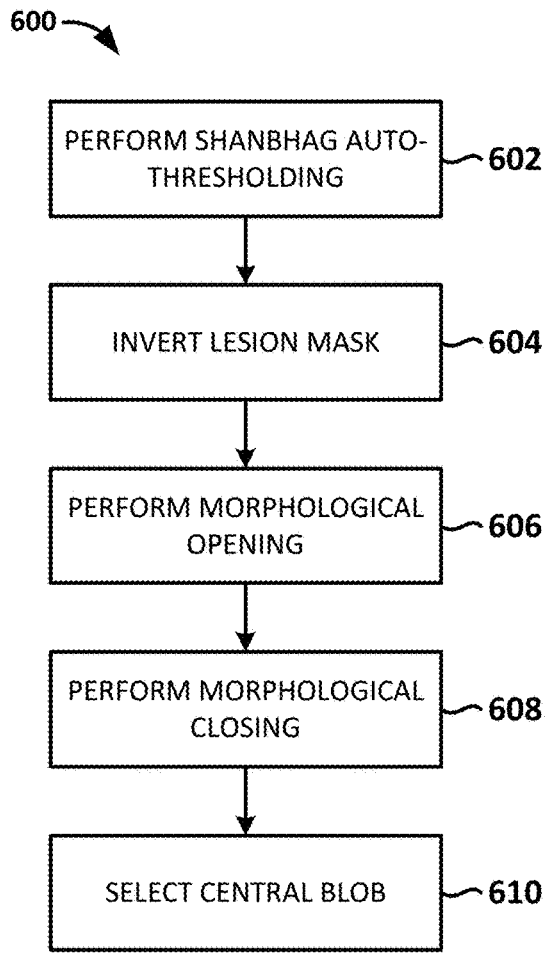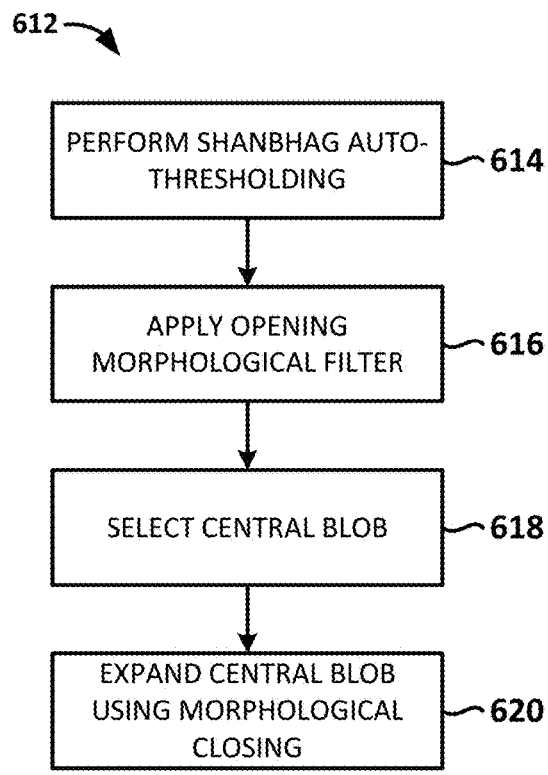
FIG. 6A
FIG. 6B

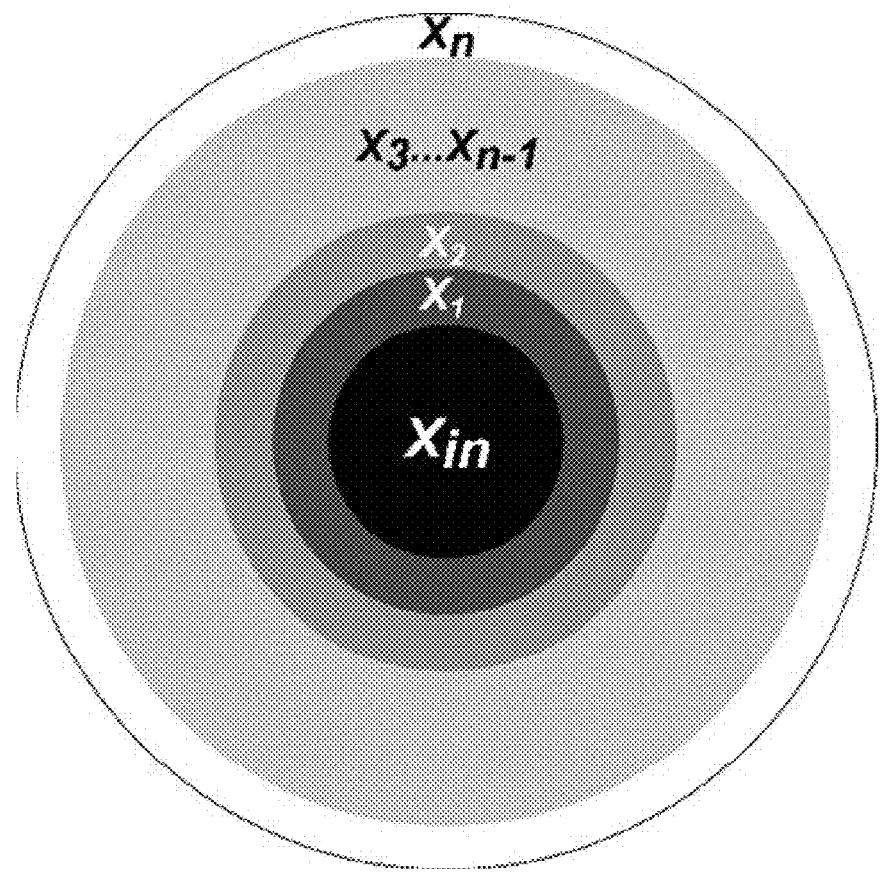
FIG. 10
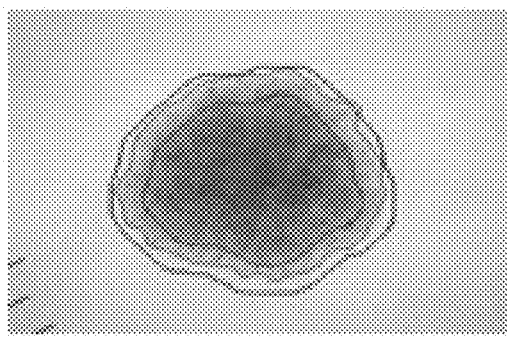 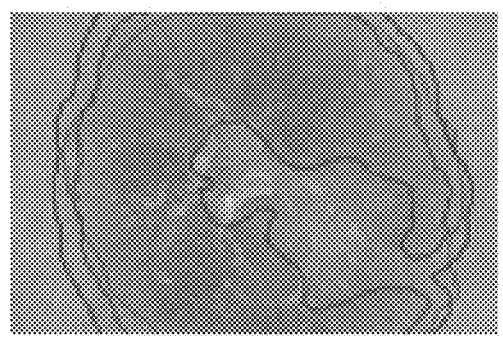
FIG. 11A　　　　　　　　　　FIG. 11B

THRESHOLDING METHODS FOR LESION SEGMENTATION IN DERMOSCOPY IMAGES

CROSS-REFERENCE

This application claims priority to U.S. Provisional Patent Application No. 62/408,603, filed Oct. 14, 2016, the entirety of which is hereby incorporated herein by reference for all purposes.

BACKGROUND

Many studies have been published concerning techniques for automation of early detection of malignant melanoma; few studies have been published for early detection of the most common skin cancer, basal cell carcinoma ("BCC"). Yet, the incidence of melanoma in the USA, an estimated 137,310 cases annually, is outnumbered nearly 20-to-1 by the estimated 2,717,097 annual cases of BCC. The growing costs of medical and surgical treatment associated with BCC are increasing the burden on healthcare systems. Because BCC often appears on the face, surgical procedures carry significant pain and potential for deformity.

Since dermoscopy images provide a fair amount of detail and are often relatively inexpensive to obtain, they provide a viable option for application of new computer vision and machine learning technologies for skin cancer detection. Therefore, automatic skin cancer detection using dermoscopy images has potential to disrupt the current clinical practice of waiting until the cancer is advanced and performing a large excision.

Dermoscopy images of skin lesions, especially of BCC, can be difficult to segment, even for dermatologists. This is due to low contrast, variations in lesion color and size, and significant aberrations and artifacts both inside and outside the lesion. To overcome these obstacles, it may be beneficial to determine a combination of robust and efficient techniques that can achieve relatively accurate segmentation. Segmentation with acceptable lesion capture and tolerance may facilitate relatively accurate feature segmentation which, in turn, may facilitate increased classification accuracy.

SUMMARY

Described herein are systems and methods that facilitate segmenting a dermoscopy image of a lesion to facilitate classification of the lesion. Generally, a dermoscopy image is received from an image source; pre-processed; and segmented. In some embodiments, segmenting the pre-processed dermoscopy image includes applying a thresholding algorithm to the dermoscopy image. The thresholding algorithm can include at least one of a Huang auto-thresholding algorithm, a Li auto-thresholding algorithm, a Shanbhag auto-thresholding algorithm, an Otsu auto-thresholding algorithm, and an Isodata thresholding algorithm.

In certain aspects, a system of the present disclosure includes an image analyzer having at least one processor that instantiates at least one component stored in a memory, the at least one component comprising: a segmenter configured to create a binary lesion mask by segmenting the dermoscopy image, the segmenter configured to segment the dermoscopy image by applying a thresholding algorithm to the dermoscopy image, the thresholding algorithm comprising at least one of a Huang auto-thresholding algorithm, a Li auto-thresholding algorithm, an Isodata auto-thresholding algorithm, a Shanbhag auto-thresholding algorithm, and an Otsu auto-thresholding algorithm. In some embodiments, the at least one component further includes a post-processing component configured to post-process the binary lesion mask by at least one of inverting the binary lesion mask, performing auto-expansion of the binary lesion mask, and applying a second order spline to the binary lesion mask.

In some embodiments, the at least one component further includes a pre-processing component configured to remove noise from the dermoscopy image, extract a blue band image from the dermoscopy image, and/or filter the dermoscopy image. The at least one component may further include a classifier configured to classify the lesion based on the one or more extracted dermatological features. The classifier may be configured to classify the lesion as a skin cancer, such basal cell carcinoma (BCC), squamous cell carcinoma (SCC), or malignant melanoma (melanoma).

In another aspect, a method of segmenting a dermoscopy image of a lesion to facilitate classification of the lesion is provided, where the method includes: receiving the dermoscopy image from an image source; pre-process the dermoscopy image; and segmenting the pre-processed dermoscopy image by applying a thresholding algorithm to the dermoscopy image, the thresholding algorithm comprising at least one of a Huang auto-thresholding algorithm, a Li auto-thresholding algorithm, and a Shanbhag auto-thresholding algorithm. In some embodiments, segmenting the pre-processed dermoscopy image includes creating a binary lesion mask, the method further comprising post-processing the binary lesion mask by inverting the binary lesion mask, performing-auto expansion of the binary lesion mask, and/or applying a second order spline to the binary lesion mask.

In some embodiments of the method, segmenting the pre-processed dermoscopy image includes creating a binary lesion mask, and further includes post-processing the binary lesion mask by at least one of inverting the binary lesion mask, performing-auto expansion of the binary lesion mask, and applying a second order spline to the binary lesion mask. In some embodiments, pre-processing the dermoscopy image includes at least one of removing noise from the dermoscopy image, extracting a blue band image from the dermoscopy image, and filtering the dermoscopy image. In certain embodiments, the method further includes extracting one or more dermatological features from the segmented dermoscopy image. The lesion may be classified based on the one or more extracted dermatological features. In some embodiments, the method includes classifying the lesion as a skin cancer or benign (e.g., classify as basal cell carcinoma (BCC), or benign (not BCC)).

In some embodiments, the thresholding algorithm of the system or method includes a Huang auto-thresholding algorithm, wherein the post-processing component is further configured to: apply an opening morphological filter; select a central blob; and expand the central blob using a closing morphological filter.

In other embodiments of the system or method, the thresholding algorithm includes a Li auto-thresholding algorithm or Isodata auto-thresholding algorithm, wherein the post-processing component is further configured to: apply an eroding morphological filter; select a central blob; and apply a convex hull.

In yet other embodiments of the system or method, the thresholding algorithm includes a Shanbhag auto-thresholding algorithm or Otsu auto-thresholding algorithm, wherein the post-processing component is further configured to: invert the lesion mask; apply an opening morphological filter to the inverted lesion mask; apply a closing morphological filter; and select a central blob. In some embodiments where the thresholding algorithm includes a Shanbhag auto-thresholding algorithm or Otsu auto-thresholding algorithm the post-processing component may alternatively be further configured to: apply an opening morphological filter; select a central blob; and expand the central blob using a closing morphological filter.

While multiple embodiments are disclosed, still other embodiments of the presently disclosed subject matter will become apparent to those skilled in the art from the following detailed description, which shows and describes illustrative embodiments of the disclosed subject matter. Accordingly, the drawings and detailed description are to be regarded as illustrative in nature and not restrictive.

BRIEF DESCRIPTION OF THE DRAWINGS

The patent or application file contains at least one drawing executed in color. Copies of this patent or patent application publication with color drawings will be provided by the Office upon request and payment of the necessary fee.

FIGS. 4, 5, 6A, and 6B are flow diagrams depicting illustrative methods of generating lesion masks for facilitating lesion classification using dermoscopy images, in accordance with embodiments of the disclosure.

FIG. 10 is a schematic diagram depicting an auto-expansion scheme, in accordance with embodiments of the disclosure.

FIGS. 11A and 11B are sample images depicting results of applying auto-expansion to lesion masks, in accordance with embodiments of the disclosure.

Figure 1:
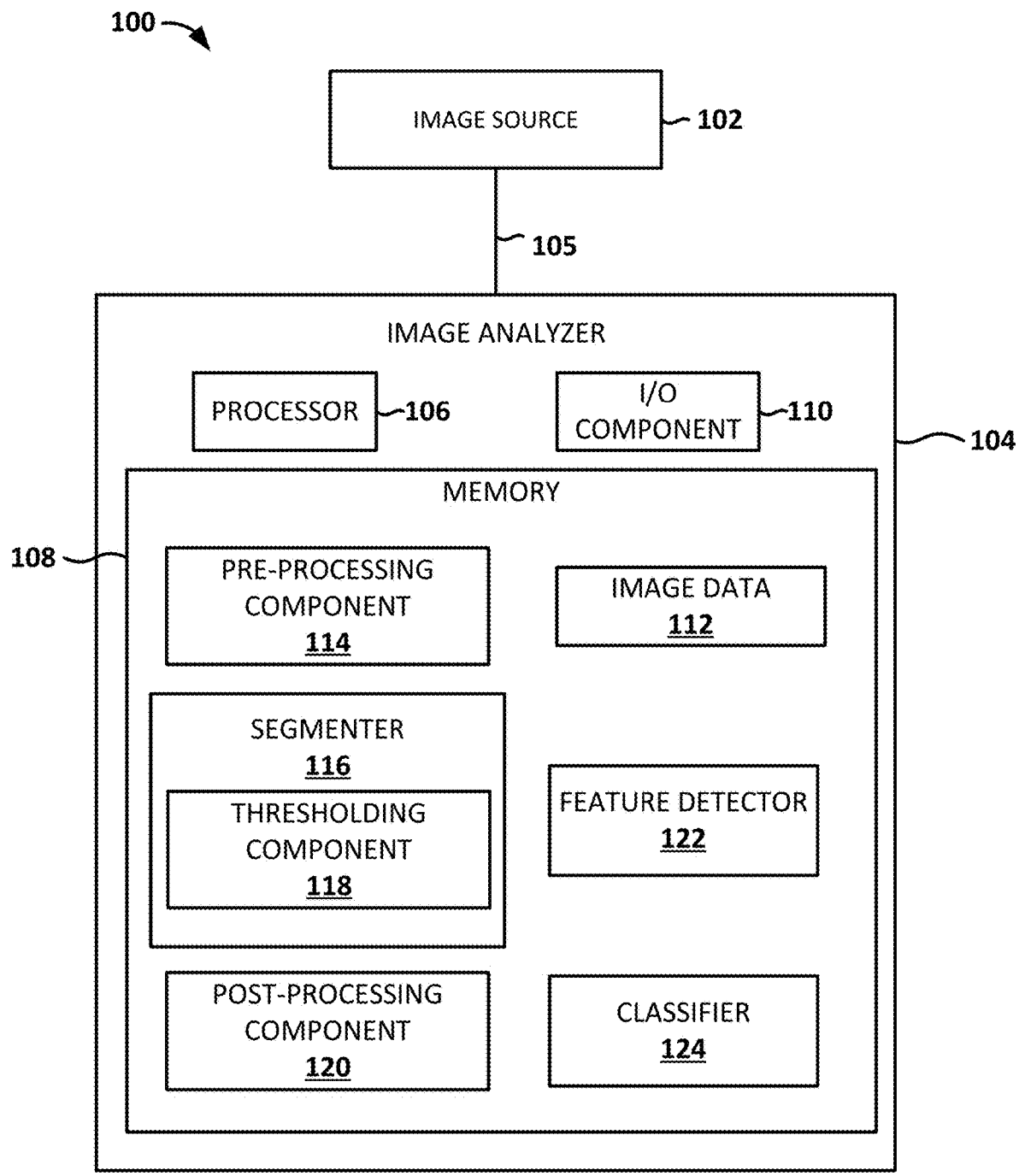
FIG. 1 is a block diagram of an illustrative digital dermoscopy system, in accordance with embodiments of the disclosure.

Although the term "block" may be used herein to connote different elements illustratively employed, the term should not be interpreted as implying any requirement of, or particular order among or between, various blocks disclosed herein. Similarly, although illustrative methods may be represented by one or more drawings (e.g., flow diagrams, communication flows, etc.), the drawings should not be interpreted as implying any requirement of, or particular order among or between, various steps disclosed herein. However, certain embodiments may require certain steps and/or certain orders between certain steps, as may be explicitly described herein, or as indicated in the drawings, and/or as may be understood from the nature of the steps themselves (e.g., the performance of some steps may depend on the outcome of a previous step). Additionally, a "set," "subset," or "group" of items (e.g., inputs, algorithms, data values, etc.) may include one or more items, and, similarly, a subset or subgroup of items may include one or more items. A "plurality" means more than one.

As the terms are used herein with respect to ranges of measurements (such as those disclosed immediately above), "about" and "approximately" may be used, interchangeably, to refer to a measurement that includes the stated measurement and that also includes any measurements that are reasonably close to the stated measurement, but that may differ by a reasonably small amount such as will be understood, and readily ascertained, by individuals having ordinary skill in the relevant arts to be attributable to measurement error, and/or differences in measurement and/or manufacturing equipment calibration, human error in reading and/or setting measurements, adjustments made to optimize performance and/or structural parameters in view of differences in measurements associated with other components, particular implementation scenarios, imprecise adjustment and/or manipulation of objects by a person or machine, and/or the like,

DETAILED DESCRIPTION

Segmentation of skin lesions is used in computer-aided diagnosis (CAD) of skin cancer. Segmentation determines a border or contour that separates the lesion from the surrounding skin, and the extraction and classification of clinical dermoscopy features, such as atypical pigment network and color, depends on the accuracy of segmentation. The contour is most commonly one picture element (pixel) wide, and is closed, completely enclosing a single undivided part of the image. The conventional goal of segmentation is to include, approximately, the skin lesion, specifically as much of the skin lesion as possible to the exclusion of surrounding skin. Success of segmentation of an image is traditionally measured by the two types of error involved: 1) the amount of the surrounding skin included within the border, measured in pixels within the image; and 2) the amount of the lesion not included within the border, measured in pixels within the image, As used herein, the term "dermoscopy" refers to a body imaging technique that involves viewing skin lesions with 8× or more magnification. The technique involves limiting surface reflectance through the use of, for example, a fluid, gel, mineral oil, or alcohol between the skin and a glass plate, or by using cross polarized light for illumination. The term "dermoscopy image" refers to a photograph of a skin lesion using a dermoscopy technique. In certain embodiments, the dermoscopy image is a digital image. Dermoscopy images may be acquired using any method known in the art, including but not limited to using specialized dermoscopy imaging platform and inexpensive digital cameras, including cameras incorporated in a smartphone, with a dermoscopy-specific attachment or lens.

FIG. 1 depicts an illustrative digital dermoscopy system 100 in accordance with embodiments of the disclosure. The digital dermoscopy system 100 includes an image source 102 that is communicably coupled to an image analyzer 104. In embodiments, the image analyzer 104 receives an image 112 from the image source 102 and analyzes the image 112 to facilitate diagnosis of a skin affliction such as, for example, BCC, SCC, or melanoma. Exemplary images include, but are not limited to, digital photographs, digital image files from medical imaging, machine vision image files, and/or the like. In embodiments, for example, the image source 102 may include a digital camera with an add-on device for 10-power magnification, and/or any other device with magnification within the range of 8-30 power. These devices may include, but are not limited to, the Canfield Epilight, Canfield Imaging Systems, Fairfield, N.J.; the 3Gen DermLite II Pro, 3Gen LLC, Dana Point, Calif.; the Heine Dermaphot, Heine Dermaphot Optics, Heine Ltd, Herrsching, Germany; and/or LED rings (3Gen Imaging, Dana Point, Calif., FotoFinder Teachscreen Software GmbH, Bad Birnbach, Germany). In embodiments, the image source 102 may be a computing device having a memory in which the image is stored.

The image source 102 is communicably coupled to the image analyzer 104 by a communication link 105. In embodiments, the image source 102 communicates an image over the communication link 105. In embodiments, the communication link 105 may be, or include, a wired communication link such as, for example, a USB link, a proprietary wired protocol, and/or the like. The communication link 105 may be, or include, a wireless communication link such as, for example, a short-range radio link, such as Bluetooth. IEEE 802.11, a proprietary wireless protocol, and/or the like. In embodiments, for example, the communication link 105 may utilize Bluetooth Low Energy radio (Bluetooth 4.1), or a similar protocol, and may utilize an operating frequency in the range of 2.40 to 2.48 GHz.

The term "communication link" may refer to an ability to communicate some type of information in at least one direction between at least two devices, and should not be understood to be limited to a direct, persistent, or otherwise limited communication channel. That is, according to embodiments, the communication link 105 may be a persistent communication link, an intermittent communication link, an ad-hoc communication link, and/or the like. The communication link 105 may refer to direct communications between the image source 102 and the image analyzer 104, and/or indirect communications that travel between the image source 102 and the image analyzer 104 via at least one other device (e.g., a repeater, router, hub, and/or the like). The communication link 105 may facilitate uni-directional and/or bi-directional communication between the image source 102 and the image analyzer 104. In embodiments, the communication link 105 is, includes, or is included in a wired network, a wireless network, or a combination of wired and wireless networks. Illustrative networks include any number of different types of communication networks such as, a short messaging service (SMS), a local area network (LAN), a wireless LAN (WLAN), a wide area network (WAN), the Internet, a peer-to-peer (P2P) network, or other suitable networks. The network may include a combination of multiple networks. In embodiments, for example, the image analyzer 104 may be accessible via the Internet (e.g., the image analyzer 104 may facilitate a web-based image analysis service), and a user may transmit an image, via the image source 102, to the image analyzer 104 for diagnostic services.

As shown in FIG. 1, the image analyzer 104 is implemented on a computing device that includes a processor 106, a memory 108, and an input/output (I/O) device 110. Although the image analyzer 104 is referred to herein in the singular, the image analyzer 104 may be implemented in multiple instances, distributed across multiple computing devices, instantiated within multiple virtual machines, and/or the like. In embodiments, the processor 106 executes various program components stored in the memory 108, which may facilitate analyzing the image 112. In embodiments, the processor 106 may be, or include, one processor or multiple processors. In embodiments, the I/O component 110 may be, or include, one I/O component or multiple I/O components and may be, or include, any number of different types of devices such as, for example, a monitor, a keyboard, a printer, a disk drive, a universal serial bus (USB) port, a speaker, pointer device, a trackball, a button, a switch, a touch screen, and/or the like. Alternatively, or additionally, the I/O component 110 may include software and/or firmware and may include a communication component configured to facilitate communication via the communication link 105, and/or the like.

Figure 2:
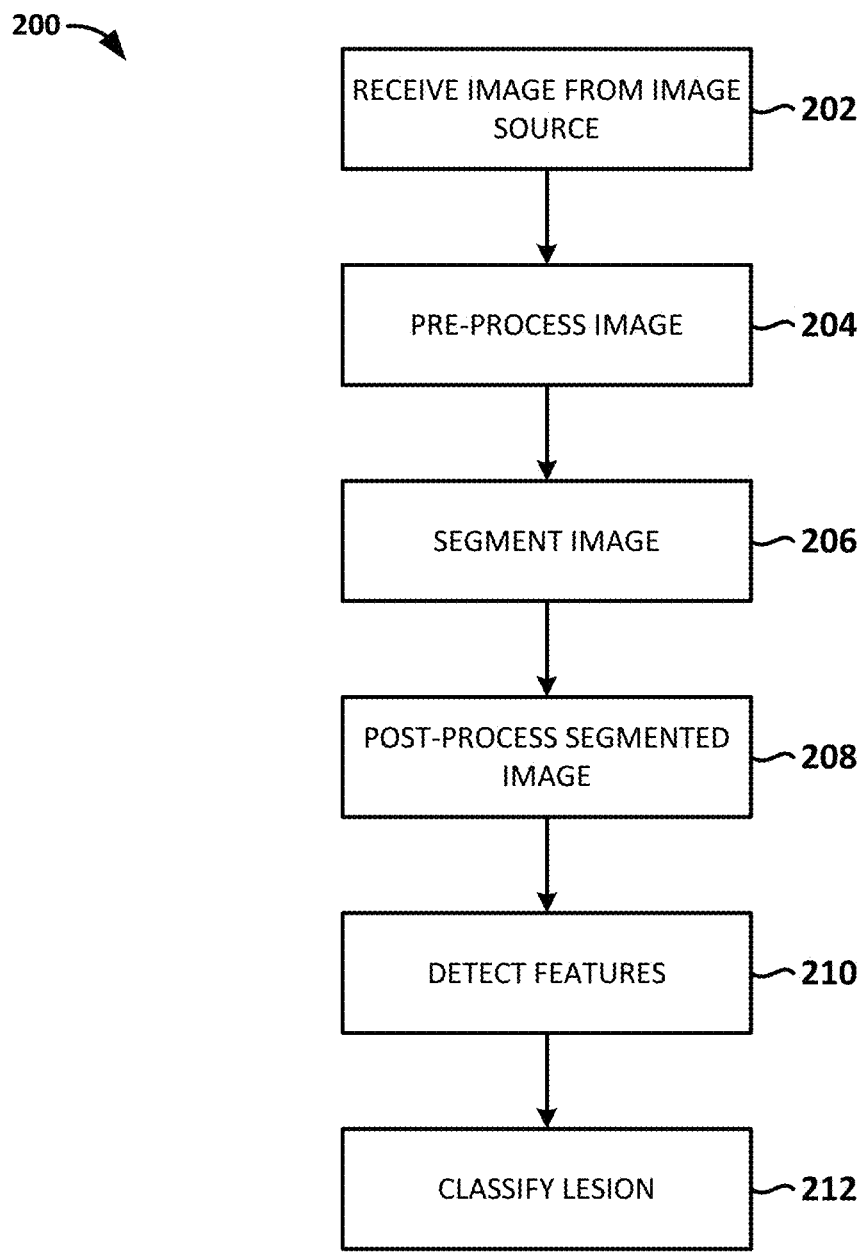
FIG. 2 is a flow diagram depicting an illustrative method of facilitating lesion classification using dermoscopy images, in accordance with embodiments of the disclosure.

According to embodiments, as indicated above, various components of the digital dermoscopy system 100, illustrated in FIG. 2, may be implemented on one or more computing devices. A computing device may include any type of computing device suitable for implementing embodiments of the invention. Examples of computing devices include specialized computing devices or general-purpose computing devices such as "workstations," "servers," "laptops," "desktops," "tablet computers," "hand-held devices," and the like, all of which are contemplated within the scope of FIG. 1 with reference to various components of the digital dermoscopy system 100. For example, according to embodiments, the image analyzer 104 (and/or the image source 102) may be, or include, a general purpose computing device (e.g., a desktop computer, a laptop, a mobile device, and/or the like), a specially-designed computing device (e.g., a dedicated video encoding device), and/or the like. Additionally, although not illustrated herein, the image source 102 may include any combination of components described herein with reference to the image analyzer 104, components not shown or described, and/or combinations of these.

In embodiments, a computing device includes a bus that, directly and/or indirectly, couples the following devices: a processor (e.g., the processor 106), a memory (e.g., the memory 108), an input/output (I/O) port, an I/O component (e.g., the I/O component 110), and a power supply. Any number of additional components, different components, and/or combinations of components may also be included in the computing device. The bus represents what may be one or more busses (such as, for example, an address bus, data bus, or combination thereof). Similarly, in embodiments, the computing device may include a number of processors, a number of memory components, a number of I/O ports, a number of I/O components, and/or a number of power supplies. Additionally any number of these components, or combinations thereof, may be distributed and/or duplicated across a number of computing devices.

In embodiments, memory (e.g., the memory 108) includes computer-readable media in the form of volatile and/or nonvolatile memory and may be removable, non-removable, or a combination thereof. Media examples include Random Access Memory (RAM); Read Only Memory (ROM); Electronically Erasable Programmable Read Only Memory (EEPROM); flash memory; optical or holographic media; magnetic cassettes, magnetic tape, magnetic disk storage or other magnetic storage devices; data transmissions; or any other medium that can be used to store information and can be accessed by a computing device such as, for example, quantum state memory, and the like. In embodiments, the memory (e.g., the memory 108) stores computer-executable instructions for causing the processor (e.g., the processor 106) to implement aspects of embodiments of system components discussed herein and/or to perform aspects of embodiments of methods and procedures discussed herein. Computer-executable instructions may include, for example, computer code, machine-useable instructions, and the like such as, for example, program components capable of being executed by one or more processors associated with a computing device. Examples of such program components include a pre-processing component 114, a segmenter 116, a thresholding component 118, a post-processing component 120, a feature detector 122, and a classifier 124. Program components may be programmed using any number of different programming environments, including various languages, development kits, frameworks, and/or the like. Some or all of the functionality contemplated herein may also, or alternatively, be implemented in hardware and/or firmware.

In embodiments, the pre-processing component 114 may be configured to pre-process an image 112 for segmentation. The pre-processing component 114 may be configured to detect and remove noises from the image such as, for example, portions of the image 112 that represent hairs, ruler markings, and/or the like. In embodiments, the pre-processing component 114 may use any number of different techniques for removing noise such as, for example, by applying an adaptive threshold for grayscale morphological closing, using an area opening filter, and applying noise removal strategies. Illustrative hair-removal techniques, among other techniques for detection of dermoscopy features, are described in U.S. Pat. No. 7,689,016, filed May 30, 2006, by William V. Stoecker et al., and entitled "AUTOMATIC DETECTION OF CRITICAL DERMOSCOPY FEATURES FOR MALIGNANT MELANOMA DIAGNOSIS," the entirety of which is hereby incorporated herein by reference for all purposes.

In an illustrative process that may be performed by the pre-processing component 114 to remove hairs, the pre-processing component 114 converts the image 112 to a modified grayscale image by processing the red plane as in steps a) and b):
a) a median filter size 3×3 is used to smooth the red plan to create the image Ir
b) The image Ir is modified by three steps i) to iii):
IrNew=Ir×(255/(255-100))
ii) IrNew1=IrNew/max(IrNew)
iii) IrNew2=255×IrNew1

The process then scans the image by a horizontal array of a certain number of pixels (e.g., 1×7 pixels), calculates a difference between the smallest pixel value and the largest pixel value of the array, and compares the calculated difference to a threshold (e.g., 15). If the difference is greater than the threshold, the pre-processing component 114 determines that the smallest pixel value indicates the presence of hair. The pre-processing component 114 may center a number of parallel, horizontally-oriented (e.g. 5×7) pixel masks on the identified hair segment and processed to generate a binary hair mask. For example, three parallel, horizontally-oriented 5×7 pixel masks may be centered on the identified hair segment, and the central mask may be replaced by the average of the two adjacent masks. The same process may be repeated on the resulting image with vertically-orientated masks, and the image resulting from this step may be subtracted from the grayscale image. The horizontal (three 5*7 rectangles horizontally oriented) and vertical masks (three 7*5 rectangles vertically oriented) are used to estimate the background. The central mask in replaced by the average of the median of the two adjacent rectangles. The grayscale image may be subtracted from the estimated background to enhance the hair [enhanced hair=(estimated background)−(grayscale image)]. The image resulting from that subtraction may be subjected to a thresholding procedure to generate a binary mask. In embodiments, the binary mask may be pruned using any number of iterations of morphological filtering to obtain a final hair mask.

According to embodiments, the pre-processing component 114 may be configured to perform a ruler mark detection algorithm. According to embodiments of the ruler mark detection algorithm, a morphological closing operation with a rectangular structuring element (e.g., 2 pixels by 50 pixels) is performed on the red plane (Ir), and a new plane is computed as:

$$Inew = Irc - Ir, \quad (1)$$

where Irc refers to the results of the closing operation, and Ir refers to the red plane. An adaptive threshold, T, is computed from Inew to find the binary image (Ib). For all (Inew)≠0, $$T = \alpha(\max(Inew)) - (\min(Inew)) + \min(Inew), \quad (2)$$

where, $\alpha = 2/5$, and may take similar values $0 < \alpha < 1$. (3)

$$Ib = \begin{cases} 1 & \text{if } Inew(x, y) > T \\ 0 & \text{otherwise} \end{cases} \quad (4)$$

Figure 18:
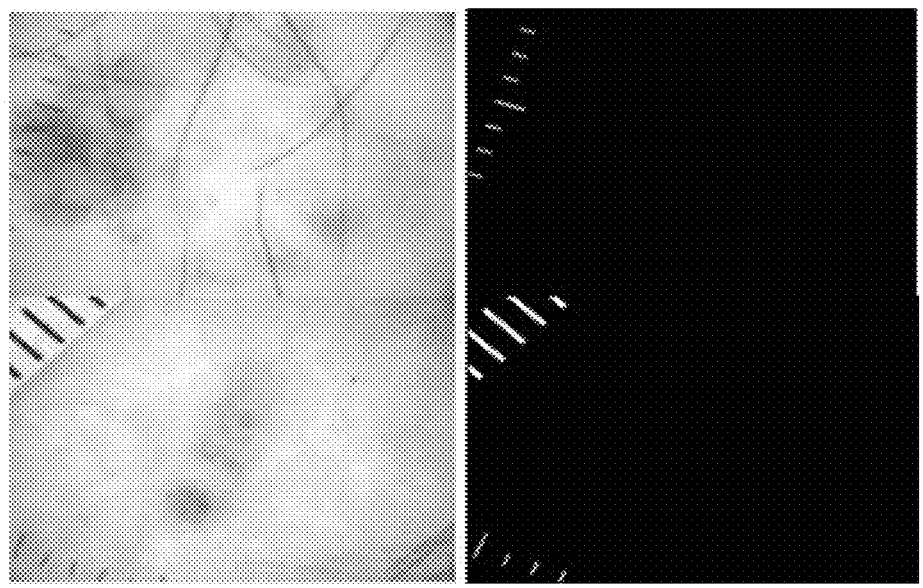

Then, Ib may be filtered using one or more filters to generate a ruler marking mask. For example, in embodiments, the Ib is filtered using two filters. In embodiments, a first filter removes all objects less than 25 pixels in length and a solidity (where solidity=Area/Convex Hull Area) of less than 0.6; and a second filter removes all objects that have their centroid inside a rectangle space (e.g., 262 pixels by 518 pixels), centered in the middle of the image. An exemplary implementation of this algorithm is depicted in FIG. 18.

Figure 19:
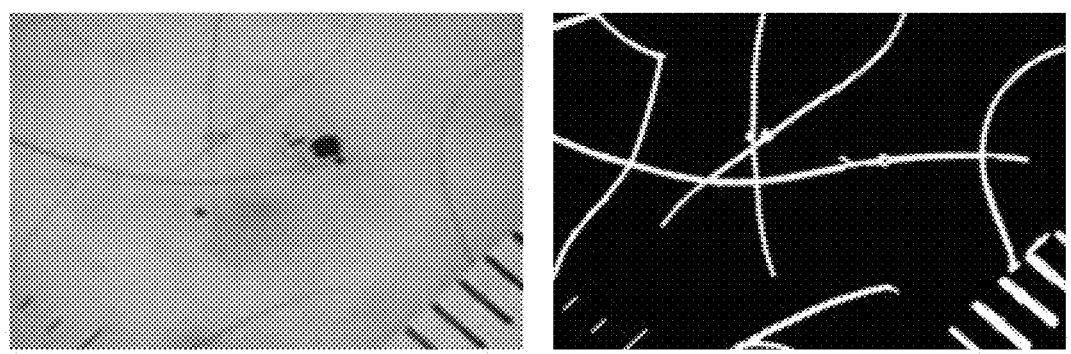
FIG. 19 includes a sample image showing hair and ruler marking artifacts (image on left) and an exemplary final pre-processing mask including both a ruler marking mask and a hair mask (image on right), in accordance with embodiments of the disclosure.

In embodiments, the ruler marking mask may be combined with a hair mask to generate final pre-processing mask. The logical OR operator may be used, for example, to overlay the ruler marking mask and the hair mask to generate the final pre-processing mask, as depicted in the exemplary implementation shown in FIG. 19.

Figure 7A:
FIG. 7A is a sample image showing hair artifacts, in accordance with embodiments of the disclosure.
Figure 7B:
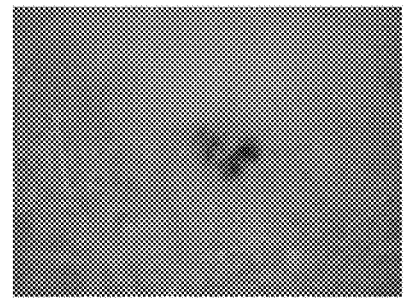
FIG. 7B is a version of the sample image depicted in FIG. 7A, in which the hair artifacts have been removed, in accordance with embodiments of the disclosure.

The pre-processing component 114 may use the final hair mask (or a final pre-processing mask, which may include other masks such as a ruler marking mask, as described above) to inpaint the RGB image 112 using linear interpolation in order to reduce the likelihood of false border detection FIG. 7A depicts a sample image with hair artifacts and FIG. 7B depicts an inpainted version of the image of FIG. 7A after hair removal. In embodiments, the hair inpainting procedure may include inpainting associated with any number of other features, including ruler markings, and/or the like. According to embodiments, the inpainting procedure may include any number of different algorithms for replacing hair (or other artifact) pixels with information from neighboring pixels, to repair and reconstruct the image without the unwanted artifacts. One illustrative algorithm is described below, though it should be understood that any number of different algorithms, modifications to the disclosed algorithm, and/or the like, may be employed to accomplish the inpainting procedure.

Figure 20:
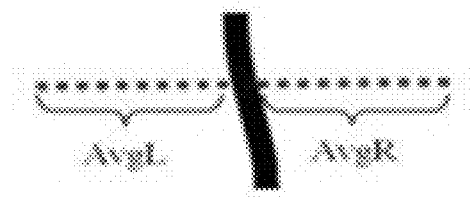
FIG. 20 depicts a portion of an inpainting algorithm, in accordance with embodiments of the disclosure, While the disclosed subject matter is amenable to various modifications and alternative forms, specific embodiments have been shown by way of example in the drawings and are described in detail below. The intention, however, is not to limit the disclosure to the particular embodiments described. On the contrary, the disclosure is intended to cover all modifications, equivalents, and alternatives falling within the scope of the disclosure as defined by the appended claims.

According to embodiments, an illustrative algorithm for inpainting includes dilating a final pre-processing mask (which may include, e.g., a final hair mask and/or a final ruler marking mask) by a disk of a specified radius (e.g., a radius of 1, 2, or 3 pixels). The remainder of the inpainting algorithm is performed in two directions, horizontal and vertical, on the R, G, and B planes separately. For each line of each plane, the averages of a set of nearby non-hair pixels (e.g., 10 nearby non-hair pixels) may be computed from the right and the left of the hair (referred to as "AvgR" and "AvgL", respectively), as depicted in FIG. 20. Embodiments of the algorithm further include constructing a vector, V, as shown below:

$$V = \begin{cases} [avgR, avgR - S, avgR - 2 \times S, \ldots, avgL] & \text{if } avgR > avgL \\ [avgR, avgR + S, avgR + 2 \times S, \ldots, avgL] & \text{otherwise} \end{cases},$$

where w is the hair width at a given line, and S=(avgR−avgL)/(w−1). In embodiments, the hair pixels in a given line are replaced using the vector V. The resulting image may be smoothed using a median filter having a specified window (e.g., 2 pixels by 2 pixels up to 25 pixels by 25 pixels).

According to embodiments, the pre-processing component 114 may apply a vignetting correction to hair-removed images in order to reduce vignetting-generated noise. Embodiments of applying the vignetting correction may include blurring the hair-removed RGB image using a filter such as, for example, a 60×60-pixel sized Gaussian lowpass filter having a sigma value of 15. The lowpass-filtered RGB-space image may be transformed to the HSV (hue, saturation and value) space image from which the value (V) plane may be extracted for further processing. The extracted V-plane may be divided into a number (e.g., 10, 15, 20, etc.) of contours using equally-separated levels of value (V). The pre-processing component 114 may determine that no vignetting effect exists if the difference between the maximum and the minimum of V is less than a certain threshold (e.g., 0.5). The central contours (those not lying at image corners) with higher V may be combined in order of higher V to lower V. Holes that are created in the process may be filled until the total area of the combined blob is greater than half the image area. An equation such as, for example, equation (14) may be used to calculate the correction index, y:

$$y = \tan h(\alpha + \tan h(x\beta\pi)), \quad (14)$$

where, α is the lowest intensity contour level in the vignetted region (image corners), β determines the steepness in the correction index y across the vignetting distance (and may be set to 0.7, for example); x is the normalized distance in the range 0 to 1, with 1 being close to the central blob, and 0 being close to the darkest region in the vignetted region. The value of y may be transformed to lie in the range 0 to 1 by using equation (15):

$$Y_p = 1 - \frac{\max(y) - y}{\max(y)}. \quad (15)$$

Figure 8A:
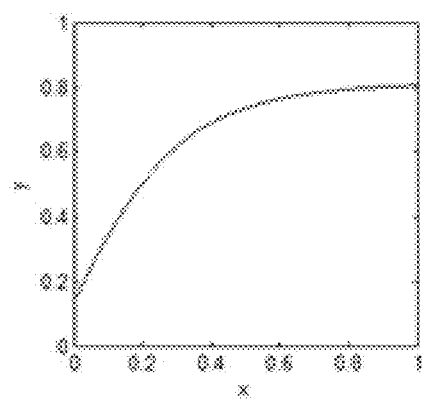
FIGS. 8A and 8B are graphs depicting a correction index curve and its normalized form, respectively, in accordance with embodiments of the disclosure.
Figure 8B:
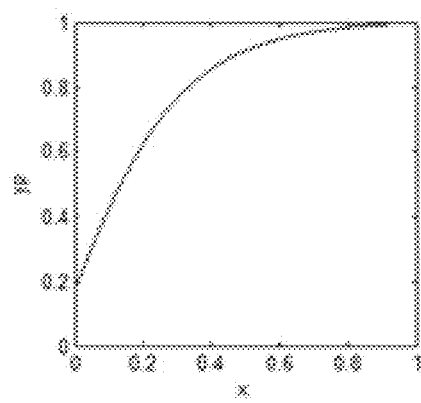

An illustrative correction index curve and its normalized form are shown in FIGS. 8A and 8B, respectively. The vignetting-corrected image shown in FIG. 8B may be achieved by dividing each pixel in R, G and B intensity planes by $Y_p$. In some embodiments, the V plane may be divided by $Y_p$. This may result in faster processing According to embodiments, the pre-processing component 114 may be configured to extract certain bands from the RGB image. That is, for example, the blue band may be extracted from the RGB image. The hair-removed blue band images may be blurred using a median filter having a window size of about 50 to about 120 to remove noise and/or interfering skin structures. In some embodiments, a median filter having a window size of about 70 may be used.

In embodiments, the segmenter 116 may be configured to segment the pre-processed image into a number of segments, defined by a lesion mask, and the post-processing component 120 may further refine the segmentation to facilitate more accurate classification of BCC and/or other types of skin lesions, including but not limited to SCC and melanoma. The segments may include, for example, objects, groups, slices, tiles, and/or the like. The segmenter 116 may employ any number of various automatic image segmentation methods known in the field. In embodiments, the segmenter 116 may use image color and corresponding gradients to subdivide an image into segments that have similar color and texture. Examples of image segmentation techniques include gradient vector flow (GVF) contours, watershed segmentation, statistical region merging (SRM), and geodesic active contours (GAC).

In embodiments, the segmenter 116 may include a thresholding component 118 that performs one or more thresholding algorithms in addition to, or in lieu of one or more other segmentation techniques such as those listed above. In embodiments where the segmenter 116 employs more than one segmentation technique, the segmenter may instantiate a classifier or other decision algorithm to determine which result to adopt, to ascertain a result that is a combination of results obtained from the multiple segmentation techniques, and/or the like. In embodiments, the segmenter 116 may utilize machine-learning techniques to train algorithms to identify appropriate segmentation techniques to select a technique based on characteristics of an image, results from pre-processing, and/or the like.

In embodiments, for example, the thresholding component 118 may utilize an image-entropy based auto-thresholding algorithm such as, for example, the Huang auto-thresholding algorithm, the Li auto-thresholding algorithm, and the Shanbhag auto-thresholding algorithm. Although other auto-thresholding algorithms may be employed, in embodiments, the Huang, Li, and Shanbhag are discussed herein, one or more of these is utilized, according to embodiments, in conjunction with one or more of the post-processing steps discussed in further detail below. Other auto-thresholding methods that may be used include, but are not limited to, the Isodata method, the Otsu method, the Mean method, the P-tile method, the Histogram Dependent Technique HDT), the Edge Maximization Technique (EMT) method, the Visual Technique method, Niblack's thresholding method, Sauvola's thresholding method, and Bernsen's thresholding method.

The Huang automatic thresholding method uses fuzzy set theory to determine the optimum threshold value t, to partition the two regions (foreground and background) of an image. The optimal t is determined by minimizing fuzziness, a measure of lack of distinction between the fuzzy set and its complement, within an image using image entropy.

As an example, consider an M×N image having L gray levels where the maximum and minimum gray levels are $g_{max}$ and $g_{min}$ respectively. Initially, $t=g_{min}$ is assigned; and average gray levels for the background and the object are calculated using (16) and (17) respectively:

$$\mu_0 = \frac{\sum_{g=0}^{t} g h(g)}{\sum_{g=0}^{t} h(g)}, \text{ and} \quad (16)$$

$$\mu_1 = \frac{\sum_{g=t+1}^{L-1} g h(g)}{\sum_{g=t+1}^{L-1} h(g)}, \quad (17)$$

where h(g) is the number of occurrences of pixels at the gray level g.

Using (16) and (17), the membership function of a pixel $x_{mn}$, for a given threshold value, is given by (18):

$$\mu_X(x_{mn}) = \begin{cases} \frac{1}{1+|x_{mn}-\mu_0|/C} & \text{if } x_{mn} \le t \\ \frac{1}{1+|x_{mn}-\mu_1|/C} & \text{if } x_{mn} > t \end{cases}, \quad (18)$$

where $C=(g_{max}-g_{min})$ and $\frac{1}{2} \le \mu_X(x_{mn}) \le 1$. The optimal threshold value is determined by minimizing the fuzziness for an image using (19):

$$E(X) = \frac{1}{MN\ln 2} \sum_g S(\mu_X(g)) h(g) \quad g = 0, 1, \ldots, L-1 \quad (19)$$

where $0 \le E(X) \le 1$ is the entropy measure and $S(\mu_X(g))$ is Shannon's function. Further optimization of the threshold value between histogram peaks is discussed in L-K. Huang and M-J. J. Wang, "Image Thresholding by Minimizing the Measure of Fuzziness," *Pattern Recognition*, vol. 28, no. 1, pp. 41-51, 1995, the entirety of which is hereby incorporated herein by references for all purposes.

Figure 9A:
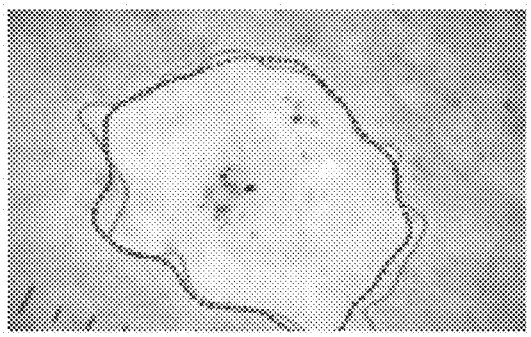
FIG. 9A is a sample image depicting a post-processed overlay for a Huang auto-thresholding algorithm, in accordance with embodiments of the disclosure.

According to embodiments, the thresholding component 118 may be configured to segment the pre-processed image using a Huang auto-thresholding algorithm employing Shannon's entropy function. Then, the post-processing component 120 may be configured to apply, to the Huang auto-thresholded image, an opening morphological filter, using a circular structuring element having a certain radius, $r_o$ (e.g., $r_o$=60). This operation may be configured to separate the central blob from the surrounding blobs. The most central large blob may be selected using the minimum Euclidian distance from the centroid of the blob to the center of the image, where a blob is considered "large" if it is one of the three largest blobs; the most central of these is considered "the most central large blob." The thresholding component 118 may be configured to expand the central blob by applying an empirically optimized morphological closing operation, using a circular structuring element of a certain radius, $r_c$ (e.g., $r_c$=70). In some embodiments, each of $r_o$ and $r_c$ can be selected from the range of 40-120. In certain embodiments, the difference between the closing and opening radii is about 10, where $r_c$ is greater than $r_o$ (e.g., $r_o$=60 and $r_c$=70). According to experimental data, the result of using opening r=60 followed by a larger closing operation r=70 was to enlarge the central blob found by the Huang method. FIG. 9A shows an example of the Huang border after performing the process described above, in which manual borders are shown with a solid line and automatic borders are shown with a dashed line.

The Li automatic thresholding method performs auto-thresholding using a fast iterative method to minimize the cross entropy of the image and the segmented version. The main criterion function developed in 1993 by Li and Lee is given by (20):

$$\eta(t) = -m_{1a}(t)\log(\mu_a(t)) - m_{1b}(t)\log(\mu_b(t)), \quad (20)$$

where, the threshold value $t \in [1, L]$, "$m_{0a}$, $m_{0b}$, $m_{1b}$ are the zeroth and first moments of the foreground and background parts of the thresholded histogram respectively" and "$\mu_a(t)$ and $\mu_b(t)$ are the portions' means", given by (21):

$$m_{0a}(t) = \sum_{i=1}^{t-1} h(i), \; m_{1a}(t) = \sum_{i=1}^{t-1} ih(i), \; \mu_a(t) = \frac{m_{1a}(t)}{m_{0a}(t)} \quad (21)$$

$$m_{0b}(t) = \sum_{i=t}^{L} h(i), \; m_{1b}(t) = \sum_{i=t}^{L} ih(i), \; \mu_b(t) = \frac{m_{1b}(t)}{m_{0b}(t)}$$

as explained in C. H. Li and P. K. S. Tam, "An Iterative Algorithm for Minimum Cross Entropy Thresholding," *Pattern Recognit. Lett.*, vol. 18, no. 8, pp. 771-776, 1998, the entirety of which is hereby incorporated herein for all purposes. The optimal threshold $t_{op}$ is calculated using (22), which minimizes η(t) for all possible threshold values:

$$t_{op} = \arg\min_t \eta(t) \quad (22).$$

A numerical method to perform this minimization with reduced computational load is proposed in C. H. Li and P. K. S. Tam, "An Iterative Algorithm for Minimum Cross Entropy Thresholding," *Pattern Recognit. Lett.*, vol. 18, no. 8, pp. 771-776, 1998; and K. E. Atkinson, "An Introduction for Minimum Cross Entropy," Wiley, New York, 1988; the entirety of each of which is hereby incorporated herein by reference for all purposes. Additionally, further details of the Li thresholding algorithm are discussed in C. H. Li and C. K. Lee, "Minimum Cross Entropy Thresholding," *Pattern Recognition*, vol. 26, no. 4, pp. 617-625, 1993, the entirety of which is hereby incorporated herein by reference for all purposes.

Figure 9B:
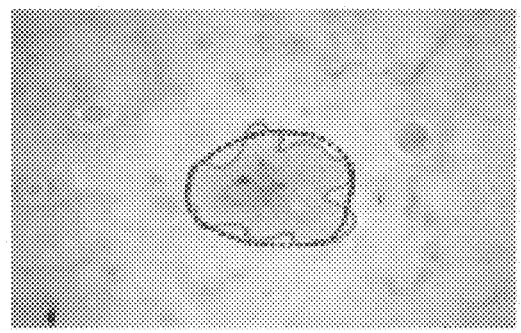
FIG. 9B is a sample image depicting a post-processed overlay for a Li auto-thresholding algorithm, in accordance with embodiments of the disclosure.

According to embodiments, the thresholding component 118 may be configured to segment the pre-processed image using a Li auto-thresholding algorithm. Then, the post-processing component 120 may be configured to apply, to the Li auto-thresholded image, an eroding morphological filter having a circular structuring element of a certain radius, $r_e$ (e.g., $r_e$=3). This small erosion operation may be configured to disconnect the central blob from the surrounding extensions. The most central large blob may be selected using the minimum Euclidian distance from the center of the blob to the center of the image, and a convex hull may be applied to avoid, or at least reduce, C-shaped objects. FIG. 9B shows an example of an image processed using the Li thresholding process described above, in which manual borders are shown with a solid line and automatic borders are shown with a dashed line.

The technique proposed by A. G. Shanbhag, "Utilization of Information Measure as A Means of Image Thresholding," *Graph. Models Image Process.*, vol. 56, no. 5, pp. 41-419, 1994, the entirety of which is hereby incorporated by reference herein for all purposes, is a modified version of the maximum entropy thresholding proposed by J. N. Kapur, et al. "A New Method for Graylevel Picture Thresholding Using the Entropy of the Histogram," *Graph. Models Image Process.*, vol. 29, no. 3, pp. 273-285, 1985, the entirety of which is hereby incorporated by reference herein for all purposes. This modified method essentially separates an image into two fuzzy sets corresponding to two classes: class 1 whose pixels range from gray levels 0 to T, and class 2 whose pixels ranging from T+1 to N, where T is the threshold value and N is the number of gray levels in the image. The membership coefficient of the gray level g is measured as an uncertainty in assigning that gray level to the specific class. An image with the leftmost and rightmost gray levels will have the maximum membership coefficient (normalized to 1) with respect to class 1 or class 2, respectively. This explains how these extreme-valued gray levels will be assigned to their respective classes, without any uncertainty.

However, as explained in Shanbhag, "hypothetical gray level T' is assumed between the threshold gray levels T and T+1, so that pixel values with the gray level of T' will have a membership coefficient of 0.5." The membership coefficient of a gray level with respect to a class also increases with the probability of occurrence of pixels with that gray level in order to obtain higher membership for pixels at larger distance from threshold within a class.

If the gray level (T−i) which is i+1 places to the left of T' has been classified as class 1, then this indicates that all pixels with the gray levels (T−i), (T−i+1), . . . , T, also have been classified as class 1. Thus, the membership of the threshold value (T−i)∈ class 1 is given as:

$$P_{1,T}(T-i) = 0.5 + k(p(T-i) + p(T-i+1) + \ldots + p(T)). \quad (23)$$

where, p(T) is the probability of occurrence of pixels with gray level T and k is a constant. By assigning the left most gray level to class 1 and using $-\log P_{1,T}(0)=0$, the value of k can be determined as, k=0.5/p(class 1).

Similarly, class 2 can be obtained with a similar calculation, using (T+i) gray level value which is i+1 places to the right of (T+1)'. The normalized class 1 distribution (such as p(0)/p(class 1), . . . p(T)/p(class 1)) is used to obtain the average amount of information by categorizing all the gray levels and is given by (24), below. Similarly, average information for class 2 is given by (25):

$$\mathrm{info}_1 = \frac{-p(0)}{p(\mathrm{class}\; 1)} \log P_{1,T}(0) - \quad (24)$$

$$\frac{p(1)}{p(\mathrm{class}\; 1)} \log P_{1,T}(1) - \ldots - \frac{p(T)}{p(\mathrm{class}\; 1)} \log P_{1,T}(T), \text{ and}$$

$$\mathrm{info}_2 = \frac{-p(N)}{p(\mathrm{class}\; 2)} \log P_{2,T}(N) - \quad (25)$$

$$\frac{p(N-1)}{p(\mathrm{class}\; 2)} \log P_{2,T}(N-1) - \ldots - \frac{p(T+1)}{p(\mathrm{class}\; 2)} \log P_{2,T}(T+1),$$

where the ideal threshold value exists when $\mathrm{info}_1 = \mathrm{info}_2$. Hence, the value of T that minimizes $|\mathrm{info}_1 - \mathrm{info}_2|$ is selected as the final threshold.

Figure 9C:
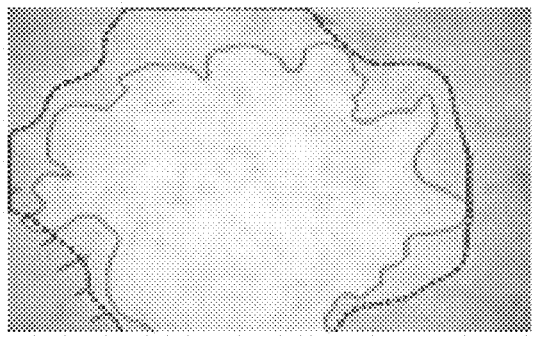
FIG. 9C is a sample image depicting a post-processed overlay for a Shanbhag Version 1 auto-thresholding algorithm, in accordance with embodiments of the disclosure.

According to embodiments, the thresholding component 118 may be configured to segment the pre-processed image using a Shanbhag auto thresholding algorithm (modified maximum entropy thresholding technique). Then, the post-processing component 120 may be configured to apply, to the Shanbhag auto-thresholded image, further processing according to, for example, a Shanbhag Version 1 and/or a Shanbhag Version 2. The Shanbhag Version 1 was initially developed to invert the segmented mask for the lesions having lighter contrast. However, this inversion may result in bigger masks that cover much of the image, as shown in FIG. 9C, in which manual borders are shown with a solid line and automatic borders are shown with a dashed line. Morphological opening and closing operations using circular structuring elements of certain radii (e.g., radii of 60 and 70) may be applied respectively, over the inverted segmented image. These two operations may be configured to prepare the mask to shrink inwards for large blobs. In one embodiment, the blob may be selected from the three largest blobs if it has the smallest Euclidian distance from the image center to the blob center. This is the blob designated "the most central large blob," and may also be designated "the central blob."

Figure 9D:
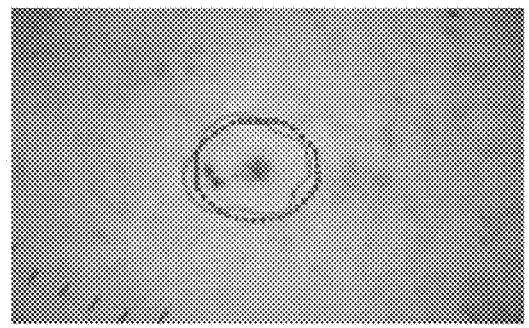
FIG. 9D is a sample image depicting a post-processed overlay for a Shanbhag Version 2 auto-thresholding algorithm, in accordance with embodiments of the disclosure.
Figure 12A:
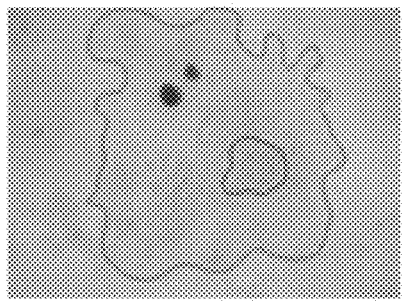
FIGS. 12A-12E are sample images depicting results of automatic GAC lesion segmentation, in accordance with embodiments of the disclosure.
Figure 12B:
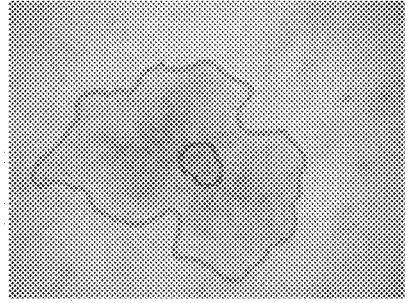
Figure 12C:
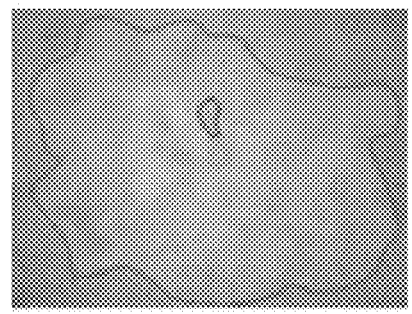
Figure 12D:
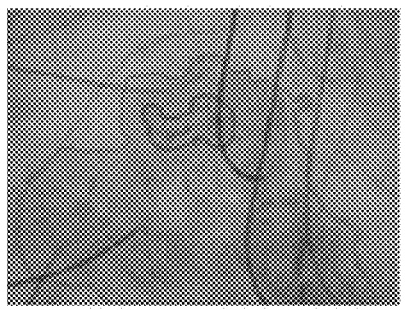
Figure 12E:
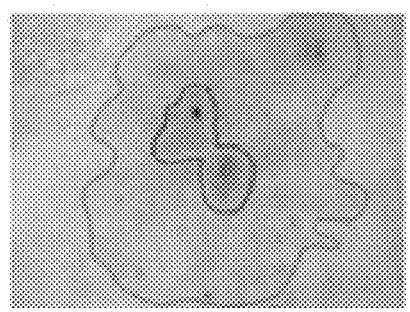

Shanbhag Version 2 includes morphological opening using a circular structuring element of a certain radius (e.g., a radius of 10), to detach the central blob from surrounding blobs. Then, the central blob may be selected using the Euclidian distance metric employed in Shanbhag Version 1. Then, the central blob may be expanded using morphological closing with circular structuring element of a certain radius (e.g., a radius of 10). An example of a post-processed Shanbhag Version 2 border is shown in FIG. 9D, in which manual borders are shown with a solid line and automatic borders are shown with a dashed line.

According to embodiments, any number of different types of border error measures may be used to assess the accuracy of the segmentation performed by the segmenter 116. In embodiments, a frequently used border error measure is the XOR error measure. Embodiments of the XOR error measure are described in M. E. Celebi, et al., "A State-of-the-Art Survey on Lesion Border Detection in Dermoscopy Images," Dermoscopy Image Analysis, M. E. Celebi, T. Mendonca and J. S. Marques, Eds., Boca Raton, CRC Press, pp. 97-129, 2015; M. E. Celebi, et al., "Lesion Border Detection in Dermoscopy Images," *Computerized Medical Imaging and Graphics*, vol. 33, no. 2, pp. 148-153, 2009; and G. A. Hance, et al., "Unsupervised Color Image Segmentation: with Application to Skin Tumor Borders," *IEEE Trans. Eng. in Med. and Bio. Mag.*, vol. 15, no. 1, pp. 104-111, January/February 1996; the entirety of each of which is hereby incorporated by reference herein for all purposes.

In embodiments of implementations of the XOR error measure, the gold standard "true border" is given as the manual border. The XOR error counts pixel disagreements between automatic and manual borders and normalizes by the manual border size. Formally, $$XOR\ Error = \frac{Area(AM \oplus MM)}{Area(MM)} = \frac{FP + FN}{TP + FN}, \quad (26)$$

where AM=Automatic border mask, MM=Manual border mask, and the ⊕ symbol means the logical XOR between the two masks. In terms of lesion pixels, TP and TN are respectively the lesion and non-lesion pixels correctly detected and FN and FP are respectively the lesion pixels falsely omitted and non-lesion pixels falsely detected, where "lesion" here indicates the true (manual) border.

Because the XOR measure under-represents FN errors and over-represents FP errors in small lesions, Sforza et al. developed the relative XOR as a measure of border inaccuracy:

Relative *XOR* Error = (27)

$$\frac{FN}{TP+FN} + \frac{FP}{FP+TN} = \left(1 - \frac{TP}{TP+FN}\right) + \left(1 - \frac{TN}{TN+FP}\right),$$

where, $$\frac{FN}{TP+FN} \text{ and } \frac{FP}{FP+TN}$$

are me FN ratio and FP ratio, respectively. Since the two fractional terms on the right in (27) represent sensitivity and specificity, the relative XOR error thus sums the fraction of the lesion missed (FN ratio=1−sensitivity) and the fraction of the non-lesional area incorrectly detected (FP ratio=1−specificity), effecting a normalization of both FP and FN error for varying lesion size. The relative XOR error is monotonically inverse to the sum of specificity and sensitivity. Further details of the relative XOR are described in G. Sforza, et al., "Using Adaptive Thresholding and Skewness Correction to Detect Gray Areas in Melanoma in Situ Images," *IEEE Trans. Instrumen. and Measure.*, vol. 61, no. 7, pp. 1839-1847, July 2012, the entirety of which is hereby incorporated by reference herein for all purposes. A drawback of this method is higher than expected FP ratio for very large lesions, a drawback partly ameliorated by the high frequency of artifacts at the image edge.

Garnavi et al. noted the greater problem presented by FN pixels, which could cause failure to identify a critical lesion feature. They advocated a new weighted border error measure:

$$W_{BorderError} = \frac{0.5FP + FN}{1.5TP + FN}, \quad (28)$$

as explained in R. Garnavi, et al., "Weighted Performance Index for Objective Evaluation of Border Detection Methods in Dermoscopy Images," *Skin Research and Technology*, vol. 17, no. 1, pp. 35-44, 2011, the entirety of which is hereby incorporated herein by reference for all purposes. The $W_{BorderError}$ numerator applies half as much weight to FP as it does to FN pixels. $W_{BorderError}$ could be optimized for a given domain by further study of FN and FP pixels.

In embodiments, in addition to the specific post-processing techniques described above with reference to each of the auto-thresholding algorithms, the post-processing component 120 may perform any number of additional post-processing procedures. For example, the post-processing component 120 may be configured to perform automatic inversion and expansion, application of splines to improve approximation of biological borders, and/or the like. That is, for example, the binary first-pass lesion masks obtained using one of more of the auto-thresholding and initial post-processing techniques described above may be processed with automatic inversion and expansion techniques such as embodiments of those described here. That is, for example, the post-processing component 120 may implement a conditional inversion process. That is, the post-processing component 120 may determine whether inversion is indicated. To do this, in embodiments, the post-processing component 120 determines whether any non-zero part of the lesion mask does not fall within a centered 101×101 block. If so, the first-pass lesion mask is inverted; and, if not, the lesion mask is not inverted. This step may facilitate accurate segmentation of lighter lesions.

According to embodiments, the conditional inversion may be followed by auto-expansion. According to other embodiments, auto-expansion may be performed where the first-pass lesion mask is not inverted. Auto-expansion may not be applied in some cases. A test, embodied in equation (29) below, is provided to determine whether auto-expansion needs be performed. The auto-expansion may be performed based on the scheme depicted in FIG. 10. The post-processing component 120 may perform embodiments of the auto-expansion technique described herein to expand the lesion border outwards by an optimized distance transform in order to include missed peripheral regions of the lesion. Embodiments of this technique automatically expand the lesion border, as shown in FIGS. 11A and 11B, based on the average of pixels inside the lesion (dark region), rims surrounding the lesion (varying gray regions) and the rest of the background (white region). The width of the first rim may be any desired width such as, for example, between 5 and 25 pixels (e.g., 5 pixels, 10 pixels, etc.). A larger rim width (e.g., 20 pixels) may be chosen to facilitate further expansion.

A basic algorithm for different levels of expansion in accordance with embodiments is described below, where a comparison of average blue plane intensity between each successive rim is performed. The inter-rim intensity differences are called jumps. Expansion continues until the jump between adjacent rims first decreases; the inner ring at this first jump decrease is included and the process halts. If the jump at the first ring exceeds an optimized K=50, the process stops; otherwise expansion continues:

$$X_{in} = \text{Mean(inner area)} \quad (29)$$
$$X_i = \text{Mean}(i^{th} \text{ ring})$$
$$\Delta X_{i+1,i} = \text{Intensity jump from } X_i \text{ to } X_{i+1}$$
$$\text{Expansion Step 1} = \begin{cases} \text{if } X_1 - X_{in} < 0, & \text{Stop (No expansion)} \\ \text{Otherwise,} & \text{Go to step 2} \end{cases}$$

$$\text{Expansion Step 2} = \begin{cases} \text{if } \Delta X_{1,in} - \Delta X_{2,1} > K, \text{ Include Ring}_1 \\ \text{Stop.} \\ \text{Otherwise, set } i = 2, \text{ go to step 3} \end{cases} \quad (30)$$

$$\text{Expansion Step 3} = \begin{cases} \text{if } \Delta X_{i+1,i} < \Delta X_{i,i-1}, \text{ Include Ring}_1 \\ \text{Stop.} \\ \text{Otherwise, set } i = i+1. \text{ If } i = n, \text{ Stop} \\ \text{Otherwise, repeat step 3} \end{cases} \quad (31)$$

The examples depicted in FIGS. 11A and 11B show the expansion outside the segmented lesion with the help of an overlay, in which the border that is generally in the inner-most position is the initial automatic mask, the border that is generally in the intermediate position (e.g., between the inner-most border and the outer-most border) is the manual border, and the border that is generally in the outer-most position is the expanded mask. In experiments, embodiments of the algorithm were able to detect only the inner-most darker lesion as the automated mask for the first image and failed to include the inlet in the second image. However, this automatic expansion technique was able to expand the mask by 4 rings (60 pixels; FIG. 11A) and 3 rings (40 pixels; FIG. 11B), thereby producing more accurate lesion masks. The reasoning for different rules in expansion steps 1 and 2 is empirical: testing on hundreds of lesions showed that special tests are needed in the first two tests outside the automatic border—first to test the brightness of the first ring in comparison to the inside brightness, and second, to test to see if the first jump exceeds the second jump by K intensity units and in that case to stop after including the first ring in the border. K is set to 50 in some embodiments.

According to embodiments, the output of either morphology or automatic expansion may result in borders having sharp corners. Accordingly, a second order spline may be applied by the post-processing component 120 to facilitate more accurate approximations of biological borders. Embodiments of application of the second order splines are described, for example, in B. Erkol, et al., "Automatic Lesion Boundary Detection in Dermoscopy Images using Gradient Vector Flow Snakes," Skin Res. Technol., vol. 11, no. 1, pp. 17-26, 2005; and R. Kasmi, et al., "Biologically Inspired Skin Lesion Segmentation Using a Geodesic Active Contour Technique," Skin Res. Technol., vol. 14, no. 3, pp. 347-353, 2011, the entirety of which is hereby incorporated herein by reference for all purposes, As is further shown in FIG. 1, and mentioned above, the image analyzer 104 further includes a feature detector 122. The feature detector may be used to detect one or more features in a segmented image. In embodiments, the feature detector 122 may represent more than one feature detector. The feature detector 122 may include any number of different types of feature detectors, implementations of feature detection algorithms, and/or the like. Examples of feature detection algorithms are shown in S. Kefel et al., Adaptable texture-based segmentation by variance and intensity for automatic detection of semitranslucent and pink blush areas in basal cell carcinoma. Skin Res Technol., 2016 Mar. 16. doi: 10.1111/srt.12281. [Epub ahead of print], P. Guvenc, et al., Region growing by sector analysis for detection of blue-gray ovoids in basal cell carcinoma. Skin Res Technol. 2013 August; 19(3):258-64. doi: 10.1111/srt.12036. Epub 2013 Jun. 1. P. Guvenc et al. Sector expansion and elliptical modeling of blue-gray ovoids for basal cell carcinoma discrimination in dermoscopy images. Skin Res Technol. 2013 February; 19(1):e532-6. doi:10.1111/srt.12006. Epub 2012 Oct. 1. S. Kefel et al. Discrimination of basal cell carcinoma from benign lesions based on extraction of ulcer features in polarized-light dermoscopy images. Skin Res Technol. 2012 November; 18(4):471-5. doi:10.1111/j.1600-0846.2011.00595.x. Epub 2012 Feb. 22. K. Ghantasala et al., The Median Split Algorithm for Detection of Critical Melanoma Color Features. VISAPP 2013, 492-495, 2013. [This is useful also for basal cell carcinoma.], B. Cheng et al., Analysis of clinical and dermoscopic features for basal cell carcinoma neural network classification. Skin Res Technol. 2013 February; 19(1):e217-22. doi: 10.1111/j.1600-0846.2012.00630.x. Epub 2012 Jun. 22. B. Cheng et al. Automatic dirt trail analysis in dermoscopy images. Skin Res Technol. 2013 February; 19(1):e20-6. doi: 10.1111/j.1600-0846.2011.00602.x. Epub 2012 Jan. 11. B. Cheng et al. Automatic telangiectasia analysis in dermoscopy images using adaptive critic design. Skin Res Technol. 2012 November; 18(4):389-96, B. Cheng et al. Automatic detection of basal cell carcinoma using telangiectasia analysis in dermoscopy skin lesion images. Skin Res Technol. 2011 August; 17(3):278-8, and W. V. Stoecker et al, Detection of basal cell carcinoma using color and histogram measures of semitranslucent areas. Skin Res Technol. 2009 August; 15(3):283-7, each of which is incorporated herein by reference in its entirety.

As is also shown in FIG. 1, the image analyzer 104 includes a classifier 124. The classifier 124 may be configured to receive input information (e.g., from the feature detector 122 and/or the post-processing component 120, and produce output that may include one or more classifications. In embodiments, the classifier may be a binary classifier and/or a non-binary classifier. The classifier may include any number of different types of classifiers such as, for example, a support vector machine (SVM), an extreme learning machine (ELM), a neural network, a convolutional neural network, logistic regression, a kernel-based perceptron, a k-NN classifier, a random forests classifier, and/or the like. The classifier 124 may be used to classify a lesion captured in an image as a BCC, an SCC, a melanoma, and/or the like.

The illustrative digital dermoscopy system 100 shown in FIG. 1 is not intended to suggest any limitation as to the scope of use or functionality of embodiments of the present disclosure. Neither should the illustrative digital dermoscopy system 100 be interpreted as having any dependency or requirement related to any single component or combination of components illustrated therein. Additionally, any one or more of the components depicted in FIG. 1 may be, in embodiments, integrated with various ones of the other components depicted therein (and/or components not illustrated), all of which are considered to be within the ambit of the presently disclosed subject matter.

As discussed above, embodiments of the disclosed subject matter include illustrative digital dermoscopy systems for facilitating lesion classification using dermoscopy images by implementing thresholding methods for segmentation of images of lesions. FIG. 2 is a flow diagram depicting an illustrative method 200 of facilitating lesion classification using dermoscopy images. Embodiments of the method 200 may be performed by aspects of the illustrative digital dermoscopy system 100 depicted in FIG. 1. As shown in FIG. 2, embodiments of the method 200 include receiving an image from image source (block 202). As described above, the image source 202 may include a digital imaging device such as, for example, a digital camera having an adapter that facilitates magnification.

Embodiments of the method 200 further include pre-processing the image (block 204). As described above, pre-processing the image may include, for example, detecting and removing noises from the image such as, for example, portions of the image that represent hairs, ruler markings, and/or the like. Pre-processing the image may also include, for example, extracting a blue band from the image, which may be an RGB image. In embodiments, the hair-removed blue band images may be blurred using a median filter to remove noise and/or interfering skin structures.

The pre-processed image is segmented (block 206) using one or more thresholding methods configured to segment the pre-processed image into a number of segments, defined by a lesion mask. According to embodiments, the thresholding methods may include, for example, image-entropy based auto-thresholding algorithms such as, for example, the Huang auto-thresholding algorithm, the Li auto-thresholding algorithm, and the Shanbhag auto-thresholding algorithm.

As shown in FIG. 2, embodiments of the method 200 further include post-processing the segmented image (block 208). For example, in embodiments in which a Huang auto-thresholding algorithm is utilized, the post-processing step may include applying, to the Huang auto-thresholded image, an opening morphological filter, selecting a central blob, and expanding the central blob by applying an empirically optimized morphological closing operation. In embodiments in which a Li auto-thresholding algorithm is utilized, the post-processing step may include applying, to the Li auto-thresholded image, an eroding morphological filter, selecting a central blob, and applying a convex hull. In embodiments in which a Shanbhag auto-thresholding algorithm is utilized, the post-processing step may include applying, to the Shanbhag auto-thresholded image, further processing according to, for example, a Shanbhag Version 1 and/or a Shanbhag Version 2, as discussed above. According to embodiments of the method 200, post-processing of an output image from any of the algorithms discussed above may include performing automatic inversion and expansion, applying splines to improve approximation of biological borders, and/or the like.

As shown in FIG. 2, embodiments of the method 200 also include detecting features in the post-processed segmented image (block 210) and classifying the lesion in the image (block 212).

Figure 3:
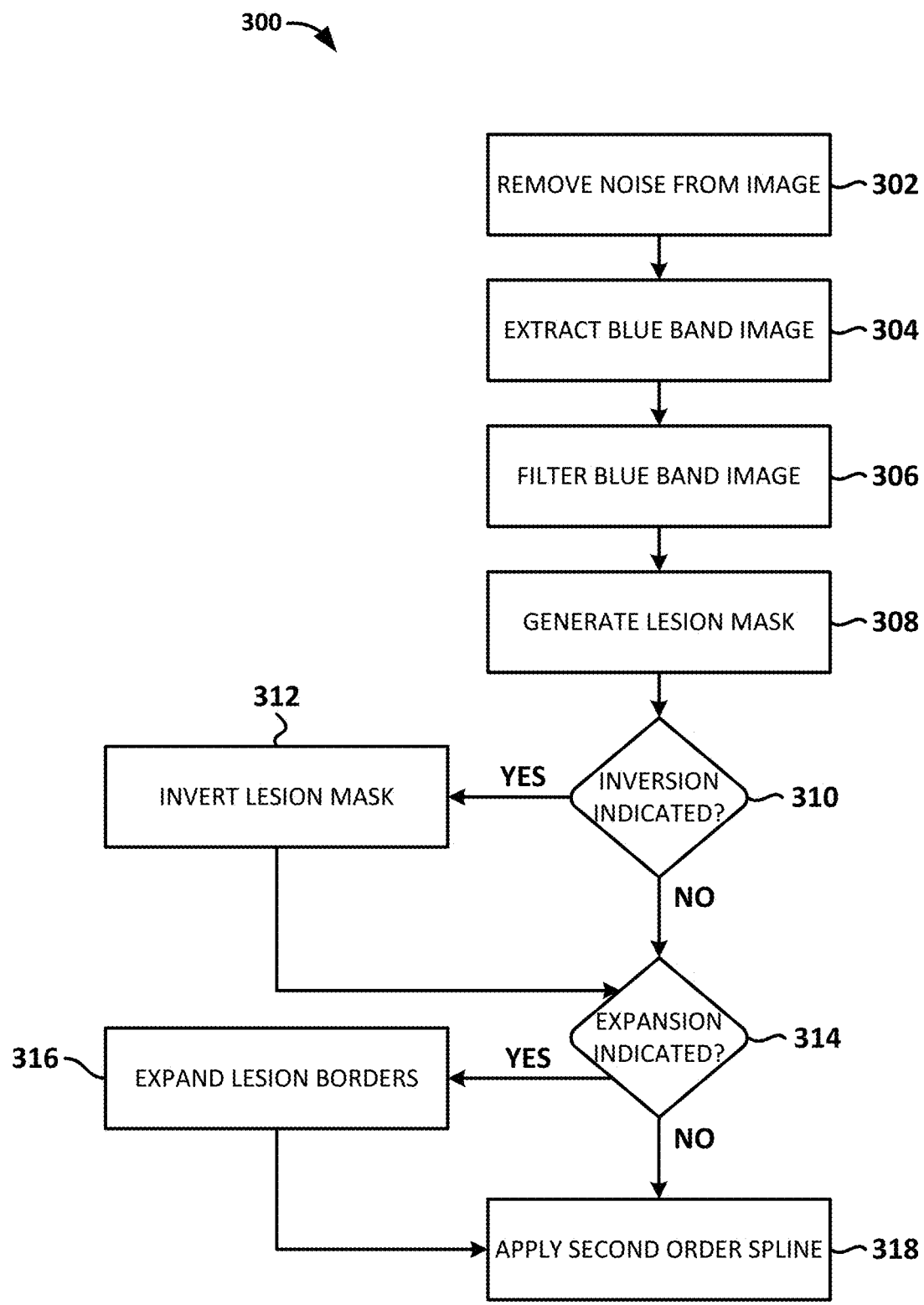
FIG. 3 is a flow diagram depicting another illustrative method of facilitating lesion classification using dermoscopy images, in accordance with embodiments of the disclosure.

FIG. 3 is a flow diagram depicting another illustrative method 300 of facilitating lesion classification using a dermoscopy image, in accordance with embodiments of the disclosure. Embodiments of the method 300 may be performed by aspects of the illustrative digital dermoscopy system 100 depicted in FIG. 1. As shown in FIG. 3, embodiments of the method 300 include pre-processing steps of removing noise from the image (block 302), extracting the blue band image (block 304), and filtering the noise-removed blue band image (block 306). In embodiments, the pre-processing steps represented by blocks 302, 304, and 306 may be performed by a pre-processing component (e.g., the pre-processing component 114 depicted in FIG. 1), and may include any number of various pre-processing techniques such as, for example, embodiments of various techniques described above with regard to the pre-processing component 114 depicted in FIG. 1.

As shown in FIG. 3, embodiments of the method 300 further include generating one or more lesion masks (block 308). Embodiments of the step of generating one or more lesion masks may include, for example, applying, to the noise-removed blue band image, one or more thresholding algorithms and, in embodiments, at least some initial post-processing techniques. In embodiments, for example, a thresholding component (e,g., the thresholding component 118 depicted in FIG. 1) may utilize an image-entropy based auto-thresholding algorithm such as, for example, the Huang auto-thresholding algorithm, the Li auto-thresholding algorithm, and the Shanbhag auto-thresholding algorithm.

Figure 4:
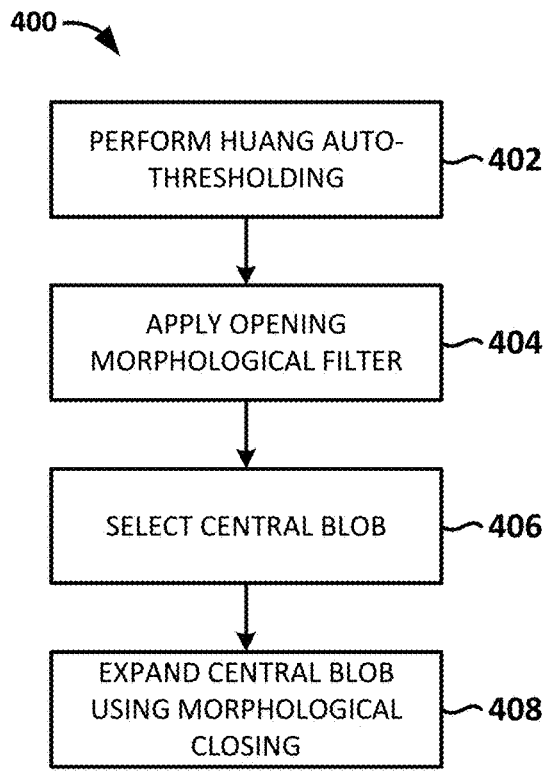
Figure 5:
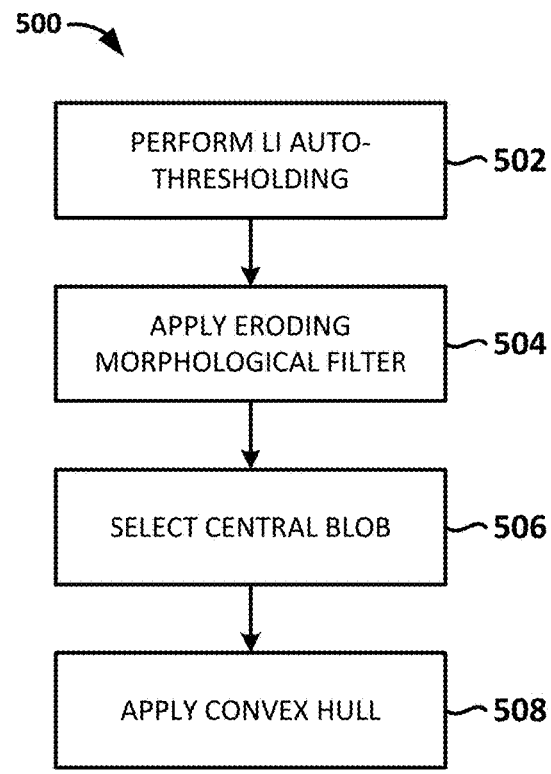

FIG. 4 is a flow diagram depicting an illustrative method 400 of generating a lesion mask using a Huang auto-thresholding algorithm and initial post-processing, in accordance with embodiments of the disclosure. As shown in FIG. 4, embodiments of the method 400 include performing a Huang auto-thresholding algorithm (block 402), as discussed herein. The method 400 may also include initial post-processing steps of applying, to the Huang auto-thresholded image, an opening morphological filter (block 404), selecting a central blob (block 406), and expanding the central blob by applying an empirically optimized morphological closing operation (block 408), FIG. 5 is a flow diagram depicting an illustrative method 500 of generating a lesion mask using a Li auto-thresholding algorithm and initial post-processing, in accordance with embodiments of the disclosure. As shown in FIG. 5, embodiments of the method 500 include performing a Li auto-thresholding algorithm (block 502), as discussed herein. The method 500 may also include initial post-processing steps of applying, to the Li auto-thresholded image, an eroding morphological filter (block 504), selecting a central blob (block 406), and applying a convex hull (block 508).

FIG. 6A is a flow diagram depicting an illustrative method 600 of generating a lesion mask using a Shanbhag Version 1 auto-thresholding algorithm, which includes a first initial post-processing technique, in accordance with embodiments of the disclosure. As shown in FIG. 6A, embodiments of the method 600 include performing a Shanbhag auto-thresholding algorithm (block 602), as discussed herein. The method 600 may also include initial post-processing steps of inverting the lesion mask that results from the auto-thresholding (block 604), performing a morphological opening operation over the inverted lesion mask (block 606), performing a morphological closing operation (block 608), and selecting the central blob (block 610).

FIG. 6B is a flow diagram depicting an illustrative method 612 of generating a lesion mask using a Shanbhag Version 2 auto-thresholding algorithm, which includes a second initial post-processing technique, in accordance with embodiments of the disclosure. As shown in FIG. 6B, embodiments of the method 612 include performing a Shanbhag auto-thresholding algorithm (block 614), as discussed herein. The method 612 may also include initial post-processing steps of applying an opening morphological filter (block 616), selecting the central blob (block 618), and expanding the central blob using a morphological closing operation (block 620).

Returning to FIG. 3, embodiments of the method 300 may include further post-processing steps including determining whether an inversion of the generated lesion mask is indicated (block 310) and, if so, inverting the lesion mask (block 312). According to embodiments, determining whether inversion is indicated may include determining whether any non-zero part of the lesion mask does not fall within a centered block (e.g., a 101×101 pixel block). If so, the lesion mask is inverted; and, if not, the lesion mask is not inverted. Embodiments of the method 300 further include determining whether expansion of lesion borders is indicated (block 314), and expanding lesion borders (block 316) using the lesion mask (if inversion was not indicated), or using the inverted lesion mask (if inversion was indicated). In embodiments, expanding the lesion borders may be performed using an auto-expansion techniques such as the auto-expansion technique discussed above with reference to the post-processing component 120 depicted in FIG. 1. A test is provided to determine whether expansion is indicated. As is further shown in FIG. 3, embodiments of the method may also include applying a second order spline (block 318), as is also discussed above with reference to the post-processing component 120 depicted in FIG. 1.

The described methods provide an optimal set of varied thresholding methods to present to a classifier, including the Huan, Li, and Shanbhag auto-thresholding algorithms. While other techniques such as Intermodes, MaxEntropy, Minimum, RenyiEntropy, Triangle, and Yen may be similarly used, the described methods may provide more inclusive borders, as measured by the weighted XOR metric. These large-enough borders are less likely to miss critical features inside lesions than other methods.

EXAMPLE

Segmentation techniques have been reported for small numbers of basal cell carcinoma images, as discussed in Q. Abbas, et al., "Lesion Border Detection in Dermoscopy Images Using Dynamic Programming," *Skin Res Technology*, vol. 17, no. 1, pp. 91-100, 2001; and Q. Abbas, et al., "Unsupervised Skin Lesions Border Detection via Two-Dimensional Image Analysis," *Computer Methods Programs Biomedicine*, vol. 104, no. 3, pp. e1-15, 2001, the entirety of each of which is hereby incorporated herein by reference for all purposes. These studies confirmed that border errors for BCC were higher than for other diagnoses. The inventors of the present disclosure sought to apply promising lesion segmentation techniques from the melanoma domain to the more challenging BCC domain. Comparison of results for different segmentation techniques is difficult because segmentation is often performed on different image sets. However, one 100-image set of borders for 30 melanomas and 70 benign lesions has been used in studies of four techniques: gradient vector flow (GVF) contours, as explained in B. Erkol, et al., "Automatic Lesion Boundary Detection in Dermoscopy Images Using Gradient Vector Flow Snakes," *Skin Res. Technol.*, vol. 11, no. 1, pp. 17-26, 2005; watershed segmentation, as explained in H. Wang, et al., "Modified Watershed Technique and Post-Processing for Segmentation of Skin Lesions in Dermoscopy Images," *Comput. Med. Imaging Graph.*, vol. 35, no, 2, pp. 116-120, 2011, the entirety of which is hereby incorporated herein by reference for all purposes; statistical region merging (SRM) (performed on 90 of the 100 images), as explained in M. E. Celebi, et al., "Border Detection in Dermoscopy Images Using Statistical Region Merging," *Skin Res. Technol.*, vol. 14, no. 3, pp. 347-353, 2011, the entirety of which is hereby incorporated herein by reference for all purposes; and geodesic active contours (GAC), as explained in R. Kasmi, et al., "Biologically Inspired Skin Lesion Segmentation Using a Geodesic Active Contour Technique," *Skin Res. Technol.*, vol. 14, no. 3, pp. 347-353, 2011. The average XOR border error (section III) for the four techniques was GVF: 15.6%, watershed segmentation: 13.6%, SRM: 11.1% and GAC 7.5%. We applied the GAC technique to BCC images and competing benign lesions. Segmentation results seen in FIGS. 12A-12E show the relatively low accuracy for the GAC technique for these images. The GAC technique often locks onto internal features and fails to find most of the lesion. To remedy this problem, we explored selected thresholding algorithms.

The inventors performed a study, in which they analyzed 1142 contact non-polarized digital dermoscopy images, each having a resolution of 1024×768. The training set (1023 images) included 305 BCCs (29.7%), median diameter=6 mm, and 718 benign images of which 292 (28.5%) were nevi, 88 (8.6%) were dysplastic nevi, 124 (12.1%) were seborrheic keratoses, and the remainder were various benign diagnoses. The separate test set of 119 images had similar percentages, e.g. 34 BCCs (28.6%). Images were acquired at four clinics as described in G. Sforza et al., "Using Adaptive Thresholding and Skewness Correction to Detect Gray Areas in Melanoma in Situ Images," *IEEE Trans. Instrumen. and Measure.*, vol. 61, no. 7, pp. 1839-1847, July 2012, the entirety of which is hereby incorporated herein by reference for all purposes, with research approved by the PCRMC Institutional Review Board (Rolla, Mo.).

Procedures for Manual and Automatic Borders

All manual lesion borders were determined by a dermatologist with 20 years' dermoscopy experience after preliminary determination by a student. Border points were smoothed by a second order spline function. Automatic border determination was developed on the 1023-image training set for all four new methods (4092 borders) and tested on the 119-image test set. Images were segmented using the ImageJ implementation of the Huang, Li, and Shanbhag automatic thresholding methods in combination with the specific pre- and post-processing routines discussed below, and coded in MATLAB 2013a.

Pre-Processing

For all automatic thresholding algorithms, the first three steps were the same. In the first step for pre-processing, hairs and similar noises like ruler markings were removed. The image was converted to grayscale and scanned by a horizontal array of 1×7 pixels; if the difference between the smallest and the largest pixel value was more than 15, the smallest pixel indicated presence of hair. Three parallel horizontally oriented 5×7 pixel masks were centered on the identified hair segment. The central mask was replaced by the average of the two adjacent masks. The exact same process was repeated on the resulting image with a vertically orientated mask. The final image was subtracted from the grayscale image and thresholded to make a binary mask. The binary mask was pruned using multiple steps of morphological filtering to obtain a final hair mask. The final hair mask was used to inpaint the RGB image using linear interpolation in order to avoid any false border detection.

A vignetting correction was applied on hair-removed images in order to circumvent vignetting-generated noise. For that purpose, the RGB image was blurred using a 60×60-pixel sized Gaussian lowpass filter and sigma value of 15, The lowpass-filtered RGB-space image was then transformed to the HSV (hue, saturation and value) space image from which the value (V) plane was extracted for further processing. The extracted V-plane was divided into 15 contours using equally-separated levels of value (V). No vignetting effect was considered to exist if the difference between maximum and minimum of V was less than 0.5. The central contours (those not lying at image corners) with higher V were combined in order of higher V to lower V. Holes that were created in the process were filled, until the total area of the combined blob was greater than half the image area. Equation (14), above, was then used to calculate the correction index, y, where, α was the lowest intensity contour level in the vignetted region (image corners), β=0.7 (determines the steepness in the correction index y across the vignetting distance, found experimentally to best fit the vignetting effect seen in dermoscopy images), x was the normalized distance in the range 0 to 1, with 1 being close to the central blob, 0 being close to the darkest region in the vignetted region. The value of y is then transformed to lie in the range 0 to 1 by using equation (15), above. The vignetting-corrected image was achieved by dividing each pixel in R, G and B intensity planes with $Y_p$), alternatively dividing each pixel in the V plane by $Y_p$.

Next the blue band was extracted from the RGB image. Testing confirmed that the best results come from using the blue band. These hair-removed blue band images were blurred using a median filter of window size 70 to remove noise and interfering skin structures, although a median filter of window size of 50 to 120 may also be used.

Post-Processing for Huang Auto-Thresholding

After the standard pre-processing steps, Huang auto-thresholding employing Shannon's entropy function was implemented. Next, an opening morphological filter was applied using a circular structuring element of radius r=60. This operation separated the central blob from the surrounding blobs. The most central large blob was selected using the minimum Euclidian distance from the center of the blob to the center of the image. The central blob was expanded by applying an empirically optimized morphological closing operation using a circular structuring element of radius 70. Larger circular structuring elements of radius up to 120 yielded no improvement. The result of using opening r=60 followed by a larger closing operation r=70 was to enlarge the central blob found by the Huang method.

Post-Processing for Li Auto-Thresholding

After pre-processing, Li auto thresholding was implemented using the fast iterative method summarized in the discussion above, with reference to FIG. 1. The segmented image was further processed by applying an eroding morphological filter having a circular structuring element of radius 3. This small erosion operation disconnects the central blob from the surrounding extensions. The most central large blob was selected using the minimum Euclidian distance from the center of the blob to the center of the image. A convex hull was applied to avoid C-shaped objects.

Post-Processing for Shanbhag Auto-Thresholding

After the standard three steps for pre-processing, the Shanbhag auto thresholding method (modified maximum entropy thresholding technique) was executed. The Shanbhag segmented image was post-processed in two different ways. The first way, Version 1, was initially developed to invert the segmented mask for the lesions having lighter contrast. However, this inversion also resulted in bigger masks that covered much of the image. Morphological opening and closing operations using circular structuring elements of radii 60 and 70 were applied respectively, over the inverted segmented image. These two operations prepared the mask to shrink inwards for large blobs. The central large blob was selected that had the smallest Euclidian distance from the image center to the blob center.

Version 2 for Shanbhag post processing included morphological opening using a circular structuring element of radius 10, to detach the central blob from surrounding blobs; then, the most central large blob is selected using the Euclidian distance metric employed in version 1. Then the central blob was expanded using morphological closing with circular structuring element of radius 10.

Post-Processing for All Algorithms

The binary first-pass lesion masks obtained using the auto-thresholding algorithms and initial post-processing steps described above were processed with automatic inversion and expansion techniques described here. The first test was to check if inversion is needed. If any non-zero part of the lesion mask does not fall within a centered 101×101 block, the first-pass lesion mask was inverted; otherwise it was not changed. This step facilitated accurate segmentation of lighter lesions. This step was followed by auto-expansion, (using the scheme shown in FIG. 10).

The auto-expansion technique was developed to expand the lesion border outwards by an optimized distance transform in order to include missed peripheral regions of the lesion. This technique automatically expands the lesion border, based on the average of pixels inside the lesion (dark region), rims surrounding the lesion (varying gray regions) and the rest of the background (white region). The width of the first two rims was chosen to be 10 pixels; if further expansion was required the subsequent expansion was performed using rim widths of 20 pixels, continuing to a maximum width of 100 pixels.

The basic algorithm for different levels of expansion is described below, where a comparison of average blue plane intensity between each successive rim is performed. The inter-rim intensity differences are called jumps. Expansion continues until the jump between adjacent rims first decreases; the inner ring at this first jump decrease is included and the process halts. If the jump at the first ring exceeds an optimized K=50, the process stops; otherwise expansion continues, using equations (29), (30), and (31), above.

The algorithm was able to detect only the innermost darker lesion as the automated mask for the first image and failed to include the inlet in the second image. However, this automatic expansion technique was able to expand the mask by 4 rings (60 pixels; see the example depicted in FIG. 11A) and 3 rings (40 pixels; see the example depicted in FIG. 11B) thereby producing more accurate lesion masks. The output of either morphology or automatic expansion resulted in borders having sharp corners; and a second order spline was used to better approximate the biological borders.

Grading of Automatic Borders to Determine ω

All 4092 automatic borders were graded by consensus of two observers—a student and a dermatologist. Automatic borders were classified in one of three groups: 1) exact (at most minute differences from the manual borders); 2) approximate (diagnosable; capturing all essential diagnostic features in the lesion); and 3) failing (either missing essential diagnostic features or capturing much of the non-lesion)

area. "Approximate" borders for the 4 methods totaled 1800:651 Huang, 627 Li, 63 Shanbhag 1 and 459 Shanbhag 2.

All approximate borders were then analyzed for FP and FN pixels within the borders. Extending the work of R. Garnavi, et al., "Weighted Performance Index for Objective Evaluation of Border Detection Methods in Dermoscopy Images," *Skin Res. Technol.*, vol. 17, no. 1, pp. 35-44, 2011, to determine the relative weights to be applied to FN and FP pixels, we propose the experimentally determined ratio of FN:FP approximate border pixels as an approximation for these relative weights. The average of this ratio over all approximate borders was 0.3334 (0.44 Huang, 0.24 Li, 0.48 Shanbhag 1 and 0.36 Shanbhag 2). This estimate for $\omega=0.3334$ is used in the results section.

Results

The relative XOR error (12) is used for the calculation of the error between the automatic and manual border. A new weighted XOR Error is defined:

$$\text{Weighted XOR Error} = (1-\omega)\left(\frac{FN}{FN+TP}\right) + \omega\left(\frac{FP}{FP+TN}\right) \quad (32)$$

Since this error measures error in capturing essential lesion features, this is termed the "Lesion Capture Ratio." For the purpose of identifying BCC in low-contrast images which often lack a distinct lesion boundary, an inclusive lesion border is more important than matching clinician borders.

Figure 13A:
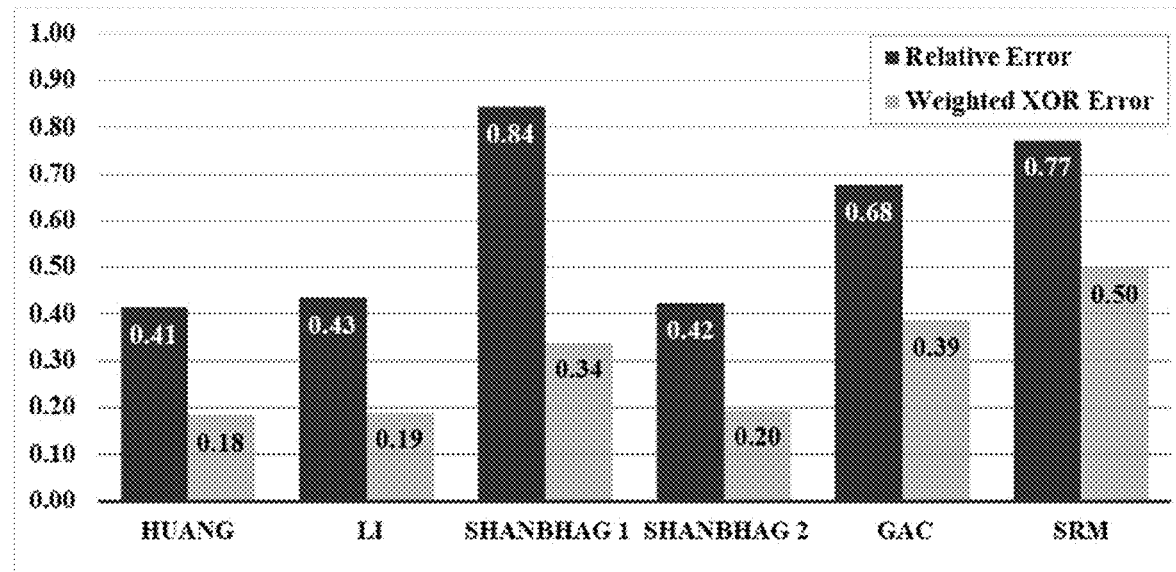
FIG. 13A is a bar graph depicting relative XOR Errors and Weighted XOR Errors for a training set, in accordance with embodiments of the disclosure.
Figure 13B:
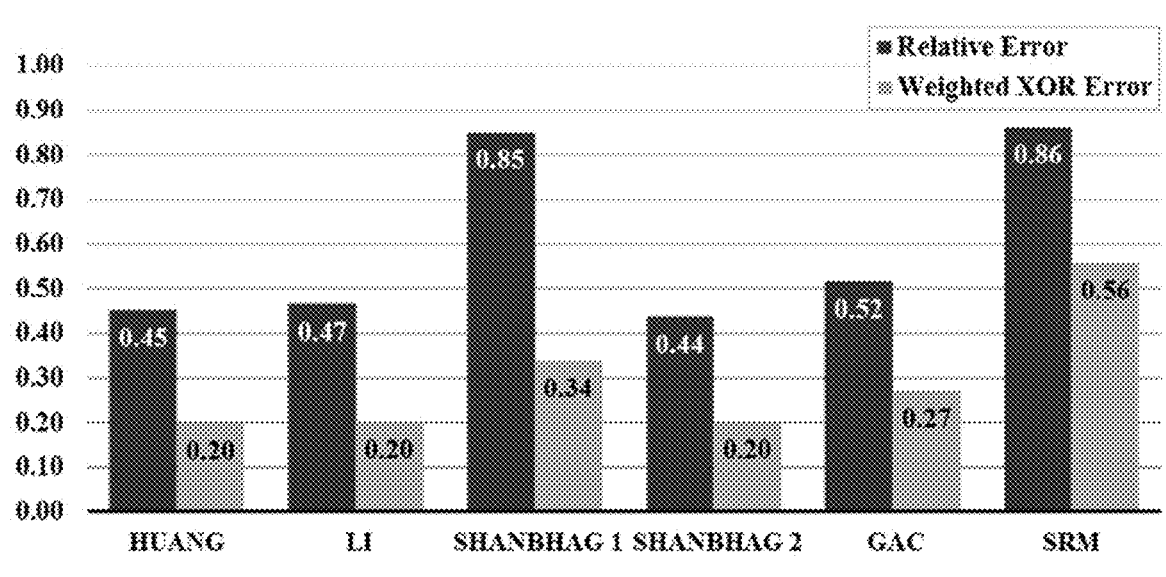
FIG. 13B is a bar graph depicting relative XOR Errors and Weighted XOR Errors for a test set, in accordance with embodiments of the disclosure.
Figure 13C:
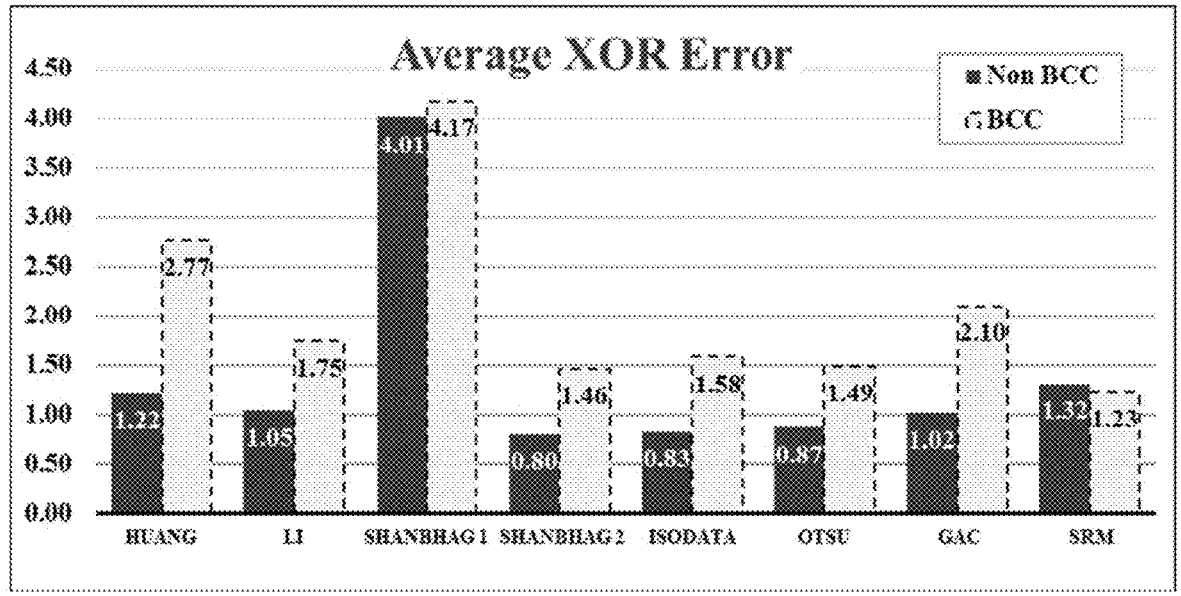
FIG. 13C is a bar graph depicting average XOR Error for a 119-image BCC Test Set, as well as a set of Non-BCC images, in accordance with embodiments of the disclosure.
Figure 13D:
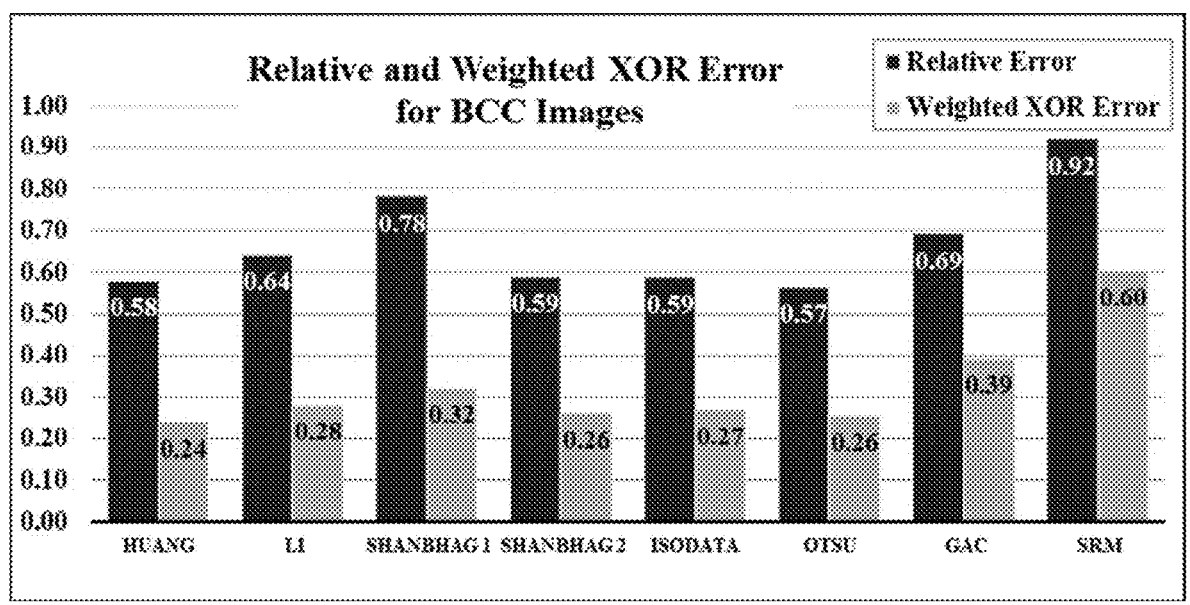
FIG. 13D is a bar graph depicting relative and weighted XOR Errors for a 119-image BCC Test Set, in accordance with embodiments of the disclosure.
Figure 14A:
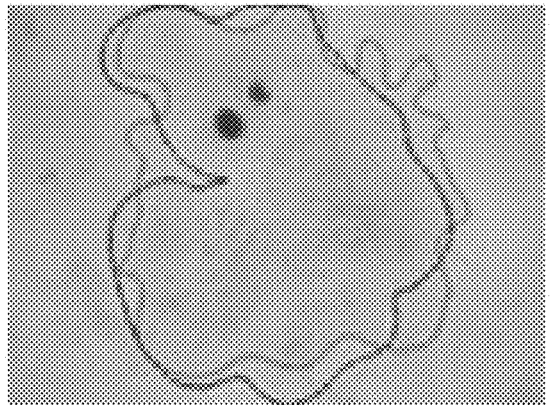
FIGS. 14A-14E are the sample images of FIGS. 12A-12E, depicting results of applying a Shanbhag Version 2 algorithm, in accordance with embodiments of the disclosure.
Figure 14B:
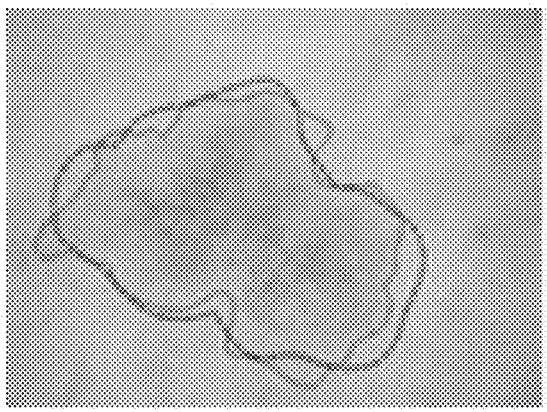
Figure 14C:
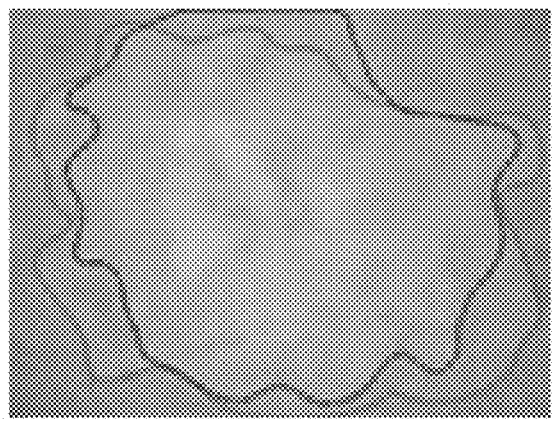
Figure 14D:
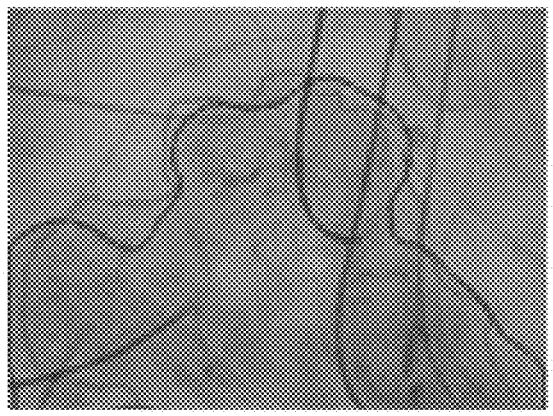
Figure 14E:
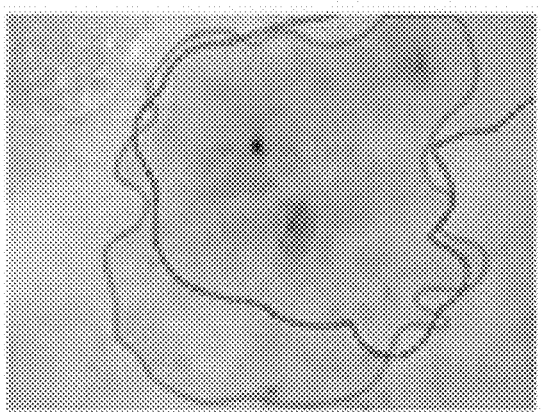

The Huang, Li, and Shanbhag 2 segmentation methods produce lower XOR, Relative XOR and Lesion Capture Ratio errors on test set images, than do the GAC and SRM methods (FIGS. 13C-13D). XOR and weighted XOR errors on the test set were similar to the errors resulting from finding borders on the training set. The SRM and GAC methods were implemented without additional training FIGS. 12A-12E show low contrast irregular borders, where the GAC mask locked onto interior noise. However, the Shanbhag 2 algorithm was able to identify the lesion border for those five images (as shown in FIGS. 14A-14E). Shanbhag 2 produced a lower test set XOR border error compared with the other five algorithms; it tied with Li and Huang for the best Lesion Capture Ratio.

Discussion

A. Thresholding Methods Selection

Figure 15:
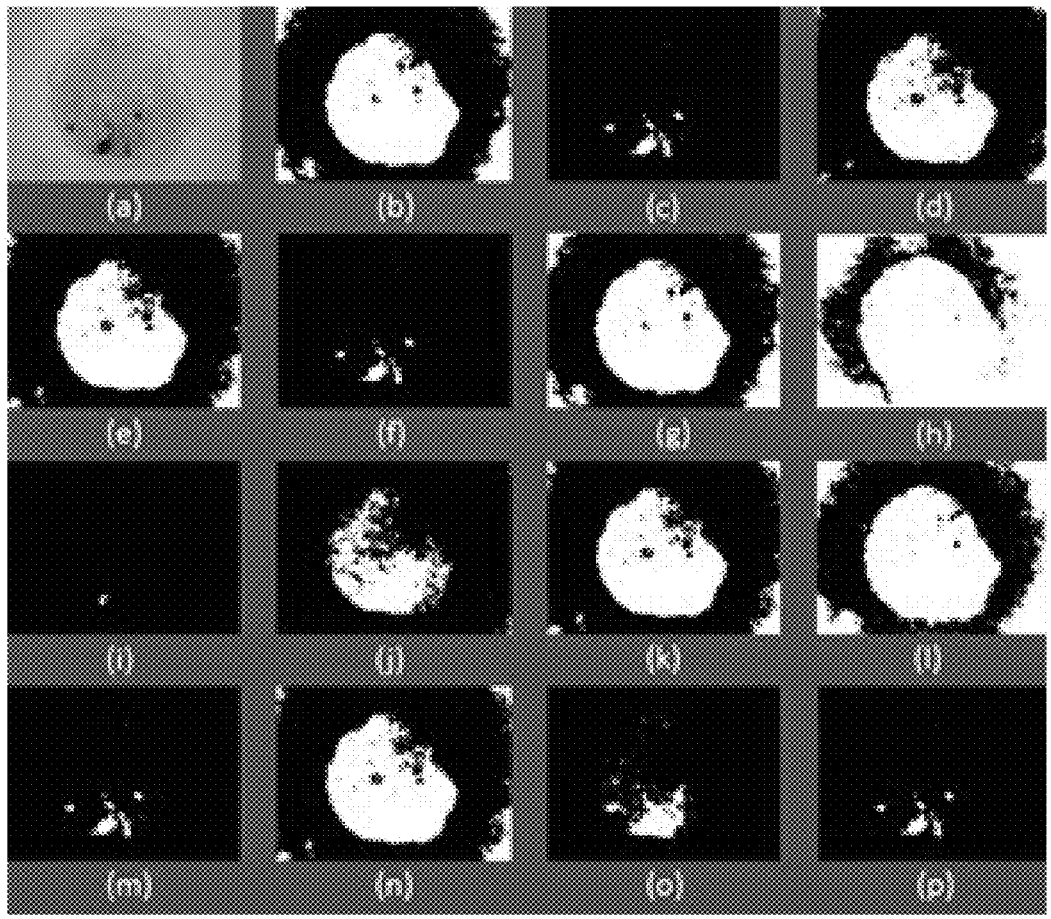
FIG. 15 depicts a manual mask overlay and mask overlays generated by various thresholding algorithms, in accordance with embodiments of the disclosure.

The 3 best thresholding algorithms were chosen from a set of 15 thresholding algorithms, available at http://fiji.sc/Auto_Threshold (last accessed Feb. 16, 2016); all 15 methods are available in ImageJ software at http://rsb.info.nih.gov/ij/download.html (last accessed Feb. 16, 2016). After implementation of these 15 methods, only 7 methods: Huang, IsoData, Li, Mean, Otsu, Percentile, and Shanbhag, thresholding methods as shown in FIG. 15 (b, d, e, g, k, l, n) respectively, produced desirable results. Other methods, Intermodes, MaxEntropy, Minimum, RenyiEntropy, Triangle, and Yen, as shown in FIG. 15 (c, f, i, m, o, p) respectively, produced blank images or blobs with small area for images with lighter lesions. Methods such as MinError and Moments shown in FIG. 15 (h, j) provided results with larger and smaller area respectively. Hence, at the beginning only 7 methods were chosen.

Figure 16:
FIG. 16 depicts manual mask overlay comparisons between a manual mask overlay, and mask overlays generated using three different thresholding algorithms without pre- or post-processing, in accordance with embodiments of the disclosure.

Out of the 7 methods that produced similar lesion borders, Percentile and Mean auto thresholding methods were not used in this research as these two methods produced lesions with larger areas that were often connected to the corners or included background area that may not be detached from the central region of interest even after vignetting correction. An example is shown in FIG. 16 where Mean and Percentile methods were compared with Huang thresholding method.

Figure 17:
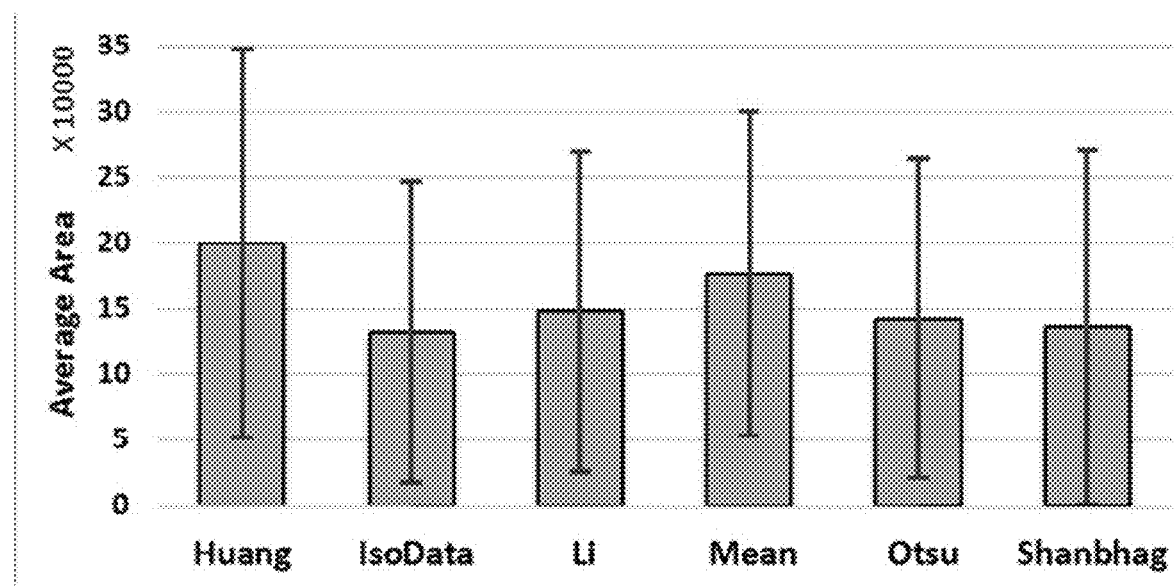
FIG. 17 is a graph depicting average area of the most central large blob selected by the minimum Euclidean distance from the image center for six thresholding algorithms, in accordance with embodiments of the disclosure, FIG. 18 includes sample images showing ruler marking artifacts (images on left) and exemplary ruler marking masks (images on right), in accordance with embodiments of the disclosure.

Apart from visual selection, the average area of the most central large blob was used to choose the best 3 methods out of the 7 candidate methods. The graph in FIG. 17 displays the average area of the most central large blob selected by the minimum Euclidian distance from the image center. IsoData and Otsu produced approximately the same average central areas which resulted in similar automatic borders as Li and Shanbhag methods, respectively. As the lesion capture ratio for Otsu and Isodata was 0.18 and 0.20 for the test images, Otsu and Isodata techniques may be substituted for Li and Shanbhag methods in other embodiments of the method.

Different post-processing methods were applied to the Otsu and Isodata techniques. Best results were obtained with the implementation shown in FIG. 6B, a flow diagram depicting an illustrative method 612 of generating a lesion mask using a Shanbhag Version 2 auto-thresholding algorithm, which includes a second initial post-processing technique, in accordance with embodiments of the disclosure. As shown in FIG. 6B, embodiments of the method 612 which include performing a Shanbhag auto-thresholding algorithm 614, as discussed herein. In comparison, the method 612 which may also include initial post-processing steps of applying an opening morphological filter 616, selecting the central blob 618, and expanding the central blob using a morphological closing operation may be applied to both the Otsu and Isodata thresholding techniques replacing the Shanbhag version 2 in FIG. 6B.

Applied to 35 BCC images, the relative XOR error for the Huang, Li, Shanbhag 2, Isodata and Otsu methods (FIGS. 13C-13D) ranges from 0.57 to 0.64; this is similar to the training set relative XOR range (0.61-0.67). Relative XOR errors for the five methods are all smaller than for GAC (0.69) and SRM (0.92).

Low-contrast and artifact-laden BCC lesions represent a truer picture of lesions found in clinics and possess borders difficult to detect, even for dermatologists. For the 119 test images, which included both BCC and non-BCC images, the average difference in XOR between two dermatologists was 33.6%, compared to the 15% difference recorded for melanoma. For all methods except SRM, XOR error for BCC was higher than for non-BCC (FIG. 13C). Using the new XOR metrics, the GAC and SRM techniques, which are accurate for pigmented lesions, did not perform as well as the five best border techniques (FIG. 13D).

B. Image Entropy Methods Best for Difficult BCC Borders

The borders of the low-contrast and artifact-laden BCC and non-melanocytic lesions, representing a truer picture of lesions in the clinic, are difficult to detect, even for dermatologists. The GAC and SRM techniques, which are relatively successful for pigmented lesions, did not perform as well as any of our best image entropy and variance techniques in this difficult domain.

C. Weighted XOR Error (Lesion Capture Ratio) and $w_{BorderError}$

To compute the weighted border error, (32), Garnavi et al. used $W_{FN}=1$, and $W_{FP}=0.5$, thus $W_{FP}=0.5*W_{FN}$. For 1023 images, our measured ratio of FN to FP pixels in adequate borders yields $\omega/(1-\omega)=0.3334/0.6666=0.5$. By penalizing the Type II error more than Type I error, this weighted XOR error measure helps in including more of the lesion on an image data set where most images lack a distinct boundary.

Many dermatologists believe exact lesion boundaries may not play a significant role in the ultimate diagnostic decision.

The described methods provide an optimal set of varied thresholding methods to present to a classifier. The advantage over other techniques is that the described methods provide more inclusive borders, as measured by the weighted XOR metric. These large-enough borders are less likely to miss critical features inside lesions than other methods.

CONCLUSION

This study presents four new thresholding methods to find borders of a challenging set of skin cancers in dermoscopy images. Three new methods compare favorably with two established border techniques. We present two new border error metrics, the relative XOR and the Lesion Capture Ratio error measures. The new border error metrics are favored over older metrics because they remove the bias against smaller lesions that some established error measures can introduce. Detection of earlier, smaller cancers is thereby facilitated.

Various modifications and additions can be made to the exemplary embodiments discussed without departing from the scope of the present disclosure. For example, while the embodiments described above refer to particular features, the scope of this disclosure also includes embodiments having different combinations of features and embodiments that do not include all of the described features. Isodata and Otsu techniques may be substituted for Li and Shanbhag techniques, respectively. Further, methods which can successfully segment BCC can be applied to any skin cancer or benign lesion. Thus descriptions of the method which recited BCC specifically are to be regarded as illustrative, as they can apply to and be extended to any skin cancer. Accordingly, the scope of the present disclosure is intended to embrace all such alternatives, modifications, and variations as fall within the scope of the claims, together with all equivalents thereof.

We claim:

1. A system for segmentation of a dermoscopy image of a lesion for facilitating classification of the lesion, the system comprising:
    an image analyzer having at least one processor that instantiates at least one component stored in a memory, the at least one component comprising:
        a segmenter configured to create a binary lesion mask by segmenting the dermoscopy image, the segmenter configured to segment the dermoscopy image by applying a thresholding algorithm to the dermoscopy image, the thresholding algorithm comprising at least one of a Huang auto-thresholding algorithm, a Li auto-thresholding algorithm, an Isodata auto-thresholding algorithm, a Shanbhag auto-thresholding algorithm, and an Otsu auto-thresholding algorithm; and
        a post-processing component configured to post-process the binary lesion mask by performing at least one of inverting the binary lesion mask, performing auto-expansion of the binary lesion mask, and applying a second order spline to the binary lesion mask;
        wherein when the thresholding algorithm includes the Huang auto-thresholding algorithm, the post-processing component is further configured to:
            apply a Huang opening morphological filter,
            select a Huang central blob, and
            expand the Huang central blob using a Huang closing morphological filter.

2. The system of claim 1, the thresholding algorithm comprising a Li auto-thresholding algorithm or Isodata auto-thresholding algorithm, wherein the post-processing component is further configured to:
    apply an eroding morphological filter;
    select a central blob; and
    apply a convex hull.

3. The system of claim 1, the thresholding algorithm comprising a Shanbhag auto-thresholding algorithm or Otsu auto-thresholding algorithm or Isodata auto-thresholding algorithm, wherein the post-processing component is further configured to:
    invert the lesion mask;
    apply an opening morphological filter to the inverted lesion mask;
    apply a closing morphological filter; and
    select a central blob.

4. The system of claim 1, the thresholding algorithm comprising a Shanbhag auto-thresholding algorithm or Otsu auto-thresholding algorithm or Isodata auto-thresholding algorithm, wherein the post-processing component is further configured to:
    apply an opening morphological filter;
    select a central blob; and
    expand the central blob using a closing morphological filter.

5. The system of claim 1, the at least one component further comprising a pre-processing component configured to perform at least one of removing noise from the dermoscopy image, extracting a blue band image from the dermoscopy image, and filtering the dermoscopy image.

6. The system of claim 1, the at least one component further comprising a feature extractor configured to extract one or more dermatological features from the segmented dermoscopy image.

7. The system of claim 6, the at least one component further comprising a classifier configured to classify the lesion based on the one or more extracted dermatological features.

8. The system of claim 7, wherein the classifier is configured to classify the lesion as a basal cell carcinoma (BCC), a squamous cell carcinoma (SCC), a malignant melanoma, or benign lesion.

9. A method of segmenting a dermoscopy image of a lesion to facilitate classification of the lesion, the method comprising:
    receiving the dermoscopy image from an image source;
    pre-process the dermoscopy image; and
    segmenting the pre-processed dermoscopy image by applying a thresholding algorithm to the dermoscopy image, the thresholding algorithm comprising at least one of a Huang auto-thresholding algorithm, a Li auto-thresholding algorithm, a Shanbhag auto-thresholding algorithm, an Otsu auto-thresholding algorithm, or an Isodata auto-thresholding algorithm, the segmenting the pre-processed dermoscopy image comprises creating a binary lesion mask; and
    post-processing the binary lesion mask by performing at least one of inverting the binary lesion mask, performing-auto expansion of the binary lesion mask, and applying a second order spline to the binary lesion mask;
    wherein when the thresholding algorithm includes the Huang auto-thresholding algorithm, post-processing the binary lesion mask includes:

applying a Huang opening morphological filter to the binary lesion mask, selecting a Huang central blob, and expanding the Huang central blob using a Huang closing morphological filter.

10. The method of claim 9, the thresholding algorithm comprising a Li auto-thresholding algorithm or Isodata auto-thresholding algorithm, wherein post-processing the binary lesion mask further comprises:

applying an eroding morphological filter to the binary lesion mask;

selecting a central blob; and applying a convex hull.

11. The method of claim 9, the thresholding algorithm comprising a Shanbhag auto-thresholding algorithm or Otsu auto-thresholding algorithm, wherein post-processing the binary lesion mask further comprises:

inverting the lesion mask;

applying an opening morphological filter to the inverted lesion mask;

applying a closing morphological filter; and selecting a central blob.

12. The method of claim 9, the thresholding algorithm comprising a Shanbhag auto-thresholding algorithm, wherein post-processing the binary lesion mask further comprises:

applying an opening morphological filter to the binary lesion mask;

selecting a central blob; and expanding the central blob using a closing morphological filter.

13. The method of claim 9, wherein pre-processing the dermoscopy image comprises performing one of removing noise from the dermoscopy image, extracting a blue band image from the dermoscopy image, and filtering the dermoscopy image.

14. The method of claim 9, further comprising extracting one or more dermatological features from the segmented dermoscopy image.

15. The method of claim 14, further comprising classifying the lesion based on the one or more extracted dermatological features.

16. The method of claim 15, wherein classifying the lesion comprises classifying the lesion as a basal cell carcinoma (BCC), a squamous cell carcinoma (SCC), a malignant melanoma, or a benign lesion.

* * * * *